United States Patent
He et al.

(10) Patent No.: US 9,890,163 B2
(45) Date of Patent: Feb. 13, 2018

(54) INHIBITORS OF PROTEIN KINASES

(71) Applicant: Princeton Drug Discovery Inc, Monmouth Junction, NJ (US)

(72) Inventors: Kan He, Princeton, NJ (US); Lining Cai, East Windsor, NJ (US)

(73) Assignee: Princeton Drug Discovery Inc, Monmouth Junction, NJ (US)

( * ) Notice: Subject to any disclaimer, the term of this patent is extended or adjusted under 35 U.S.C. 154(b) by 0 days.

(21) Appl. No.: 15/516,355

(22) PCT Filed: Oct. 11, 2016

(86) PCT No.: PCT/US2016/056439
§ 371 (c)(1),
(2) Date: Mar. 31, 2017

(87) PCT Pub. No.: WO2017/066193
PCT Pub. Date: Apr. 20, 2017

(65) Prior Publication Data
US 2017/0240545 A1    Aug. 24, 2017

Related U.S. Application Data

(60) Provisional application No. 62/241,903, filed on Oct. 15, 2015, provisional application No. 62/400,510, filed on Sep. 27, 2016.

(51) Int. Cl.
| | | |
|---|---|---|
| C07D 401/02 | (2006.01) | |
| C07D 401/14 | (2006.01) | |
| C07D 401/10 | (2006.01) | |
| A61K 31/437 | (2006.01) | |
| A61K 31/4353 | (2006.01) | |
| C07D 471/04 | (2006.01) | |

(52) U.S. Cl.
CPC .................. *C07D 471/04* (2013.01)

(58) Field of Classification Search
CPC .. C07D 401/14; C07D 401/02; C07D 401/10; A61K 31/437; A61K 31/4353
USPC .......................... 546/119, 121; 514/300, 303
See application file for complete search history.

(56) References Cited

U.S. PATENT DOCUMENTS

| | | | |
|---|---|---|---|
| 7,504,509 B2 | 3/2009 | Ibrahim et al. | |
| 7,863,288 B2 | 1/2011 | Ibrahim et al. | |
| 8,143,271 B2 | 3/2012 | Ibrahim et al. | |
| 8,202,876 B2 | 6/2012 | Albaugh et al. | |
| 8,288,540 B2 | 10/2012 | Chianelli et al. | |
| 8,377,636 B2 | 2/2013 | Haley et al. | |
| 8,426,404 B2 | 4/2013 | Zhang et al. | |
| 8,470,818 B2 | 6/2013 | Ibrahim et al. | |
| 8,741,920 B2 | 6/2014 | Hildbrand et al. | |
| 2010/0048552 A1 | 2/2010 | Ren et al. | |
| 2011/0053932 A1 | 3/2011 | Sim et al. | |
| 2013/0245039 A1 | 9/2013 | Higgins et al. | |
| 2013/0303534 A1 | 11/2013 | Ibrahim et al. | |
| 2016/0235723 A1 | 8/2016 | Hilgeroth | |
| 2016/0347755 A1 | 12/2016 | Gray et al. | |
| 2017/0014396 A1 | 1/2017 | Gu | |

FOREIGN PATENT DOCUMENTS

| | | | |
|---|---|---|---|
| WO | 2012109075 | * | 8/2012 |
| WO | 2017066193 A1 | | 4/2017 |

OTHER PUBLICATIONS

Barker KT, et al. "BRK Tyrosine Kinase Expression in a High Proportion of Human Breast Carcinomas" Oncogene 1997, vol. 15, pp. 799-805.
Harvey A, et al. (2011) "Future Therapeutic Strategies: Implications for Brk Targeting," Breast Cancer—Current and Alternative Therapeutic Modalities, Prof. Esra Gunduz (Ed.), InTech, DOI: 10.5772/23991. Available from: https://www.intechopen.com/books/breast-cancer-current-and-alternative-therapeutic-modalities/future-therapeutic-strategies-implications-for-brk-targeting.
Zeng H, et al. "Discovery of Novel Imidazo[1,2-a]pyrazin-8-amines as Brk/PTK6 Inhibitors" Bioorganic & Medicinal Chemistry Letters 2011, vol. 21, pp. 5870-5875.
Miah S, et al. "BRK Targets Dok1 for Ubiquitin-Mediated Proteasomal Degradation to Promote Cell Proliferation and Migration" PLoS ONE 2014, vol. 9, No. 2: e87684. doi:10.1371/journal.pone.0087684.
Mizuguchi Y, et al. "Breast Tumor Kinase/Protein Tyrosine Kinase 6 (Brk/PTK6) Activity in Normal and Neoplastic Biliary Epithelia" Journal of Hepatology 2015, vol. 63, pp. 399-407.
Mahmoud KA, et al. "Novel Inhibitors of Breast Cancer Relevant Kinases Brk and HER2" Med. Chem. Commun. 2014, vol. 5, pp. 659-664.
Mahmoud KA, et al. "Discovery of 4-Anilino alpha-Carbolines as Novel Brk Inhibitors" Bioorganic & Medicinal Chemistry Letters 2014, vol. 24, pp. 1948-1951.
Ono H, et al. "PTK6 Promotes Cancer Migration and Invasion in Pancreatic Cancer Cells Dependent on ERK Signaling" PLoS ONE vol. 9, No. 5: e96060. doi:10.1371/journal.pone.0096060.
Pires IM, et al. "Hif-1α-Independent Hypoxia-Induced Rapid PTK6 Stabilization is Associated with Increased Motility and Invasion" Cancer Biology & Therapy 2014, vol. 15, No. 10, pp. 1350-1357.
Elkins JM et al. "Comprehensive Characterization of the Published Kinase Inhibitor Set" Nature Biotechnology (published online Oct. 26, 2015) doi:10.1038/nbt.3374, pp. 1-11.
Goel R, et al. "Tracing the Footprints of the Breast Cancer Oncogene BRK—Past Till Present" Biochimica et Biophysica Acta 2015, vol. 1856, DOI 10.1186/s13058-015-0594-z, pp. 39-54.

(Continued)

*Primary Examiner* — Niloofar Rahmani
(74) *Attorney, Agent, or Firm* — Thomas F. Woolf

(57) ABSTRACT

Protein kinases are regulators of cellular signaling and their functional dysregulation is common in carcinogenesis and many other disease states or disorders. The present invention relates to novel chemical entities that have biological activity to modulate mammalian protein kinase enzymes. In particular, compounds of the invention display potent inhibition of breast tumor related kinase (BRK).

8 Claims, No Drawings

(56) References Cited

OTHER PUBLICATIONS

Park SH, et al. "PTK6 Inhibition Promotes Apoptosis of Lapatinib-Resistant Her2+ Breast Cancer Cells by Inducing Bim" Breast Cancer Research 2015, vol. 17: 86 (pp. 1-13).

Peng M, et al. "Protein Tyrosine Kinase 6 Promotes ERBB2-Induced Mammary Gland Tumorigenesis in the Mouse" Cell Death and Disease 2015, vol. 6, e1848; doi:10.1038/cddis.2015.210 (pp. 1-8).

Noble MEM, et al. "Protein Kinase Inhibitors: Insights into Drug Design from Structure" Science 2004, vol. 303, pp. 1800-1805.

* cited by examiner

INHIBITORS OF PROTEIN KINASES

CROSS REFERENCE TO RELATED APPLICATIONS

This application is a national stage filing under 35 U.S.C. § 371 of PCT International Application PCT/US2016/056439 designating the United States of America, and filed Oct. 11, 2016 the entire contents of which are hereby incorporated herein by reference. This application claims the benefit under 35 U.S.C. § 119(e) to U.S. Provisional Application No. 62/241,903, filed on Oct. 15, 2015, the entire contents of which is incorporated herein by reference.

FIELD OF THE INVENTION

The present invention relates to novel chemical entities that have biological activity to modulate mammalian protein kinase enzymes.

BACKGROUND OF THE INVENTION

The information provided herein is intended solely to assist the understanding of the reader. None of the information provided nor references cited is admitted to the prior art to the present invention. Each of the references cited herein is incorporated in its entirety.

The identification of the molecular events that underlie the development of human tumors presents a major challenge in the design of improved strategies in the prevention, management, and cure of these diseases (Barker, K. T. et al. BRK Tyrosine Kinase Expression in a High Proportion of Human Breast Carcinomas, Oncogene 1997, 15:799-805). The role of aberrantly regulated protein tyrosine kinases (PTKs) in human tumor development is the subject of intense investigation (Barker id.).

Protein kinases are regulators of cellular signaling and their functional dysregulation common in carcinogenesis and many other disease states or conditions (Mizuguchi, Y. et al., Breast Tumor Kinase/Protein Tyrosine Kinase 6 (Brk/PTK6). J Hepatology 2015, 63, 399-407; Mahmoud, K. A. et al., Discovery of 4-Anilino α-Carbolines as Novel Brk Inhibitors. Bioorganic & Medicinal Chemistry Letters 2014, 24:1948-1951: Nobel, M. E. M. Protein Kinase Inhibitors: Insights into Drug Design from Structure. Science 2004, 303:1800-1805). The human genome encodes over 500 protein kinases that share a catalytic domain conserved in sequence and structure but which are notably different in how their catalysis is regulated (Nobel id.). Protein kinases regulate key signal transduction cascades that control or are involved in the control of physiological functions including cellular growth and proliferation, cell differentiation, cellular development, cell division, stress response, transcription regulation, aberrant mitogenesis, angiogeneisis, abnormal endothelial cell-cell or cell-matrix interactions during vascular development, inflammation, Jun-N-terminal kinase (JNK) signal transduction, and several other cellular processes (see U.S. Pat. No. 8,470,818). Protein kinase inhibitors have been established as promising drugs that inhibit overactive protein kinases in cancer cells (Mahmoud id.).

A partial, non-limiting list of these kinases includes: BRK, FGR, PDGFRα(V561D), DDR2, LYNa, SRM, PDGFRα, LCK, DDR1, KDR, ACK, JAK1, LYNb, KIT, CSK, YES, KIT(V560G), BLK, MST1, JAK2, RET (S891A), SRC, FYN(isoform a), RET(G691S), FYN(isoform b), PDGFRβ, RET, FLT4, RET(Y791F), skMLCK, FRK, MST2, FLT1, AurA, FLT3, JAK3, RET(M918T), WNK3, p388, FGFR2, MNK1, MNK2, PIK3CA/PIK3R1, PDGFRα(D842V), MET, FGFR1, BRAF(V600E), MAP2K5, KIT(D816E), ALK, FGFR3, RAF1, MAP2K3, HER4, KIT(D816V), Erk5, EGFR, YES(T348I), KIT (V654A), KIT(D816Y), PDGFRα(T674I), BRAF, ABL, HER2, EPHA5, ROCK2, KIT(T670I), PKD3, MST4, MAP2K1, MAP2K2, MST3, ROCK1, IGF1R, PKD2, MAP2K6, Erk2, PKD1, MAP2K7, Erk1, MAP2K4, and BTK (see U.S. Pat. No. 8,470,818 B2 for detailed information on kinase nomenclature and biological properties). Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-related diseases or conditions.

SUMMARY OF INVENTION

The present invention concerns compounds active on protein kinases in general.

In one aspect, the present invention provides a compound having formula I:

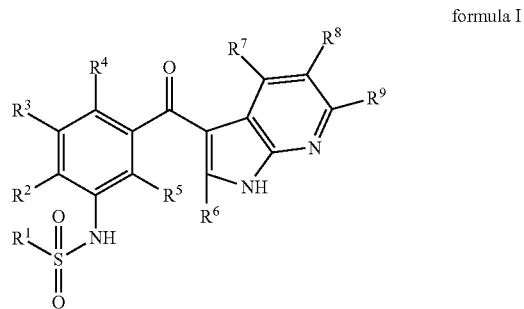

formula I all salts, prodrugs, tautomers and isomers thereof. In some embodiments of formula I, $R^1$ is a substituted lower alkyl or lower alkenyl, wherein the lower alkyl or lower alkenyl is substituted with one or more substituents selected from —OH, =O, and alkoxy; and $R^2$, $R^3$, $R^4$, $R^5$, $R^6$, $R^7$, $R^8$, and $R^9$ are independently selected from the group consisting of hydrogen, halogen, optionally substituted lower alkyl, optionally substituted lower alkenyl, optionally substituted cycloalkyl, optionally substituted heterocycloalkyl, optionally substituted aryl, optionally substituted heteroaryl, —CN, and —NO₂.

In one aspect, the present invention provides a compound having formula II:

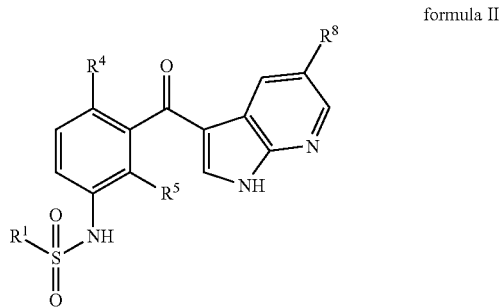

formula II all salts, prodrugs, tautomers and isomers thereof. In some embodiments of formula II, $R^1$ is a substituted lower alkyl or lower alkenyl, wherein the lower alkyl or lower alkenyl is substituted with one or more substituents selected from —OH, =O, and alkoxy; and $R^4$, $R^5$, and $R^8$ are independently selected from the group consisting of hydrogen, halogen, optionally substituted lower alkyl, optionally substituted lower alkenyl, optionally substituted cycloalkyl, optionally substituted heterocycloalkyl, optionally substituted aryl, optionally substituted heteroaryl, —CN, and —NO₂.

In one aspect, the present invention provides a compound having formula III:

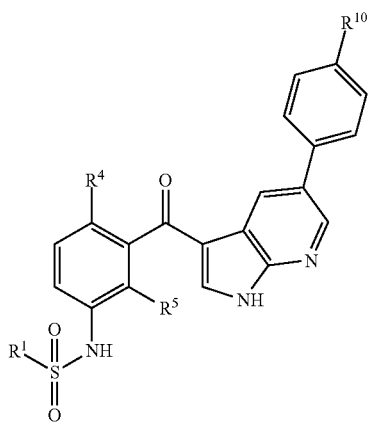

formula III all salts, prodrugs, tautomers and isomers thereof. In some embodiments of formula III, $R^1$ is a substituted lower alkyl or lower alkenyl, wherein the lower alkyl or lower alkenyl is substituted, with one or more substituents selected from —OH, =O, and alkoxy; and $R^4$, $R^5$, and $R^{10}$ are independently selected from the group consisting of hydrogen, halogen, optionally substituted lower alkyl, optionally substituted lower alkenyl, optionally substituted cycloalkyl, optionally substituted heterocycloalkyl, optionally substituted aryl, optionally substituted heteroaryl, —CN, and —NO₂.

In one aspect, the present invention provides a compound having formula IV:

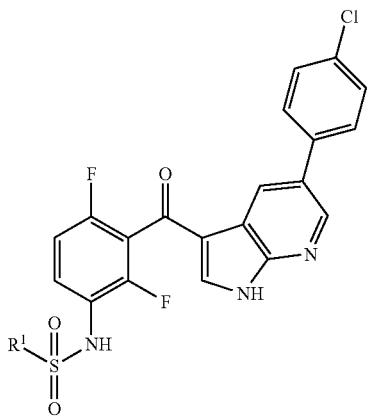

formula IV all salts, prodrugs, tautomers and isomers thereof. In some embodiments of formula III, $R^1$ is a substituted lower alkyl or lower alkenyl, wherein the lower alkyl or lower alkenyl is substituted with one or more substituents elected from —OH, =O, and alkoxy.

In one aspect, the present invention provides compound having the structure of 200-17:

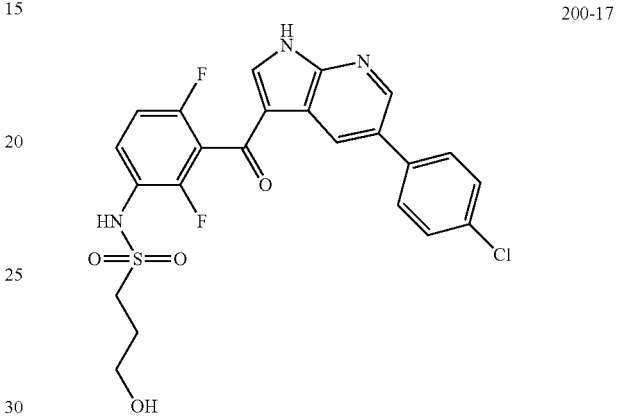

200-17 all salts, prodrugs, tautomers, and isomers thereof.

In another aspect, the present invention provides a compound having the structure of 200-73:

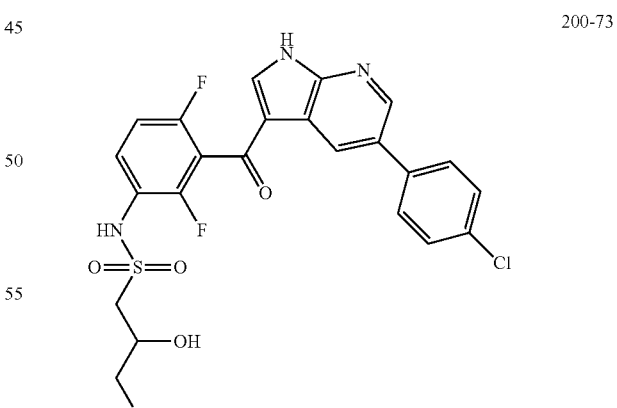

200-73 all salts, prodrugs, tautomers, and isomers thereof.

In another aspect, the present invention provides a compound having the structure of formula 200-93:

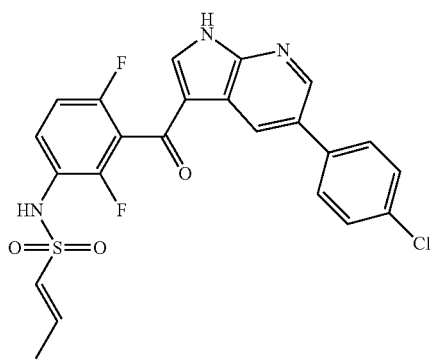

200-93 all salts, prodrugs, tautomers, and the cis and trans isomers (200-93a and 200-93b) thereof.

In another aspect, the present invention provides a compound having the structure of formula 200-115:

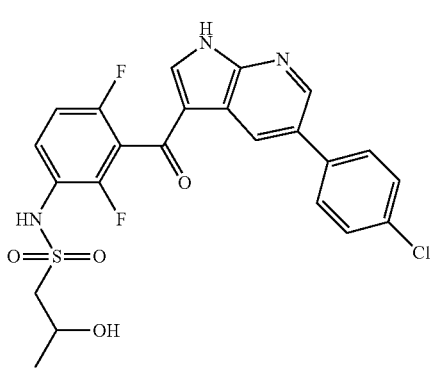

200-115 all salts, prodrugs, tautomers, and isomers thereof.

In another aspect, the present invention provides a compound having the structure of 200-117:

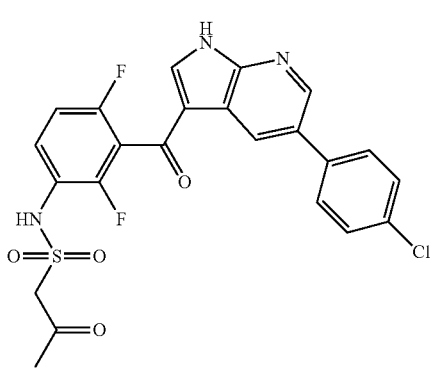

200-117 all salts, prodrugs, tautomers, and isomers thereof.

In another aspect, the present invention provides a compound having the structure of 200-123:

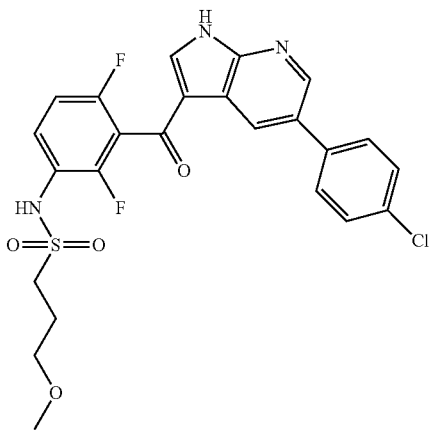

200-123 all salts, prodrugs, tautomers, and isomers thereof.

In another aspect, the present invention provides a compound having the structure of 200-139:

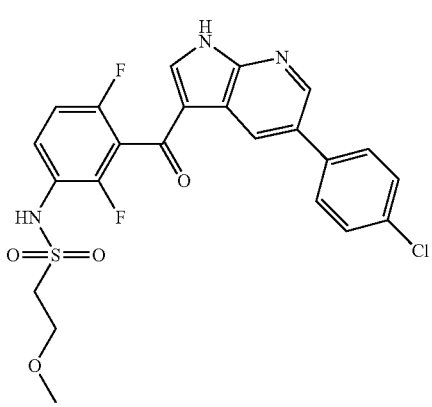

200-139 all salts, prodrugs, tautomers, and isomers thereof.

In another aspect, the present invention provides a compound having the structure of 200-149:

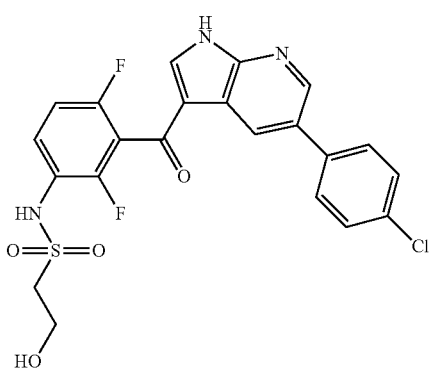

200-149 all salts, prodrugs, tautomers, and isomers thereof.

In one aspect, the invention provides a method for treating a protein kinase-mediated disease or condition in an animal or human subject wherein the method involves administering to the subject an effective amount of formulas I, II, III, or IV, 200-17, 200-73, 200-93, 200-93a, 200-93b, 200-115, 200-117, 200-123, 200-139 or 200-149. The terms "treat," "therapy," and like terms refer to the administration of compounds in an amount effective to prevent, alleviate, or ameliorate one or more symptoms of a disease condition, i.e., indication, and/or to prolong the survival of the subject being treated. The term "protein kinase-mediated disease or condition" refers to a disease or condition in which the biological function of a protein kinase affects the development, course, and/or symptoms of the disease or condition. A protein kinase-mediated disease or condition includes a disease or condition for which modulation provides a positive effect, i.e., one in which treatment with protein kinase inhibitors, including compounds described herein, provides a therapeutic benefit to the subject with or at risk of the disease or condition.

In one aspect, the invention provides a method for treating a breast tumor related kinase (BRK) mediated disease or condition in a mammal, wherein the method involves administering to the subject an effective amount of a compound of the invention. BRK is also known as protein tyrosine kinase 6 (PTK6). The term BRK mediated disease or condition refers to a disease or condition in which the biological function of BRK, including any mutations thereof, affects the development, course, and/or progression of the disease or condition, and/or in which modulation of BRK alters the development, course, and/or symptoms of the disease or condition. BRK includes, but is not limited to, BRK and mutations of BRK.

The compounds of formula I, II, III, or IV, 200-17, 200-73, 200-93, 200-93a, 200-93b, 200-115, 200-117, 200-123, 200-139 or 200-149 described herein may be administered in an effective amount. An "effective amount" or "therapeutically effective amount" is an amount of a preparation that alone, or together with further doses, produces the desired response. Desired response may involve: (1) halting the progression of the disease or condition, (2) delaying the onset of the disease or condition, and (3) preventing the disease or condition from occurring, although it may also imply only slowing of the disease or condition.

In reference to compounds of the invention, specification of a compound or group of compounds includes pharmaceutically acceptable salts, prodrugs(s), and all isomers (cis/trans; enantiomers, and diasteriomers) of such compounds.

In one aspect, the invention provides for pharmaceutical compositions that include a therapeutically effective amount of a compound of formulas I, II, II, or IV, 200-17, 200-73, 200-93, 200-93a, 200-93b, 200-115, 200-117, 200-123, 200-139 or 200-149 in free form or in a pharmaceutically acceptable salt form and at least one pharmaceutically acceptable carrier, excipient, and/or diluent.

DETAILED DESCRIPTION OF THE INVENTION

Definitions

As used herein the following definitions apply unless clearly indicated otherwise: By "chemical structure" or "chemical substructure" is meant any definable atom or group of atoms that constitute an individually identifiable portion of a molecule, such as a substituent moiety, a core which is optionally substituted, and the like. Normally, chemical substructures of a ligand can have a role in binding of the ligand to a target molecule, or can influence, the three-dimensional shape, electrostatic charge, and/or conformational properties of the ligand.

The term "prodrug" is a compound that, upon in vivo administration, is metabolized by one or more steps or processes or otherwise converted to the biologically, pharmaceutically, or therapeutically active form of the compound. To produce a prodrug, the pharmaceutically active compound is modified such that the active compound will be regenerated by metabolic processes.

The term "binds" in connection with the interaction between a target and a potential binding compound indicates that the potential binding compound associates with the target to a statistically significant degree as compared to association with proteins generally (i.e., non-specific binding).

As used herein the term "modulating" or "modulate" refer to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) its activity. This type of activity is typically indicated in terms of an inhibitory concentration ($IC_{50}$) for an inhibitor or an excitation concentration ($EC_{50}$) for an activator.

As used herein in connection with compounds of the invention, the term "synthesizing" and like terms means chemical synthesis from one or more precursor materials. Further, by "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

The term "lower alkyl" is art-recognized, and includes saturated aliphatic groups, including straight-chain alkyl groups and branched-chain alkyl groups. In certain embodiments, a straight-chain or branched-chain alkyl has about 6 or fewer carbon atoms in its backbone (e.g., C1-C6 for straight chain, C3-C6 for branched chain).

The term "lower alkenyl" refers to an unsaturated straight or branched hydrocarbon having at least one carbon-carbon double bond, such as a straight or branched group 2 to 6 carbon atoms, referred to herein as C2-C6 alkenyl.

The term "cycloakyl" refers to a 3 to 7 membered monocyclic ring of aliphatic groups, including C3-C7, that is optionally substituted with alkyl, alkenyl, alkoxyl, or optionally substituted amino, halogens, cyano (—CN), or nitro (—$NO_2$).

The term "aryl" alone or in combination refers to a monocyclic or bicyclic ring system containing aromatic hydrocarbons such as phenyl or naphthyl, which may be optionally fused with a cycloalkyl of preferably 5 to 7 carbon atoms, more preferably 5 to 6 carbon atoms.

The term "heterocycloalkyl" refers to a saturated or unsaturated 5 non-aromatic cycloalkyl group having from 5 to 10 carbon atoms in which from 1 to 3 carbon atoms in the ring are replaced by heteroatoms of O, S, or N, and are optionally fused with benzo or heteroaryl of 5 to 6 ring members.

The term "alkoxyl" or "alkoxy" are art-recognized and refer to an alkyl group, as defined above, having an oxygen radical attached thereto. Representative alkoxyl groups include methoxy, ethoxy, propyloxy tert-butoxy, and the like.

The term "substituted amines" moiety that may be represented as $NR_2$ where R is independently hydrogen or alkyl.

"Halogen" refers to chloro (Cl), fluoro (F), bromo (Br), or iodo (I).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures.

The term "pharmaceutically acceptable" means that the indicated material does not have properties that would cause a reasonably prudent medical practitioner to avoid administration of the material to a patient, taking into consideration the disease or condition to be treated and the respective route of administration. For example, it is commonly required that such a material be essentially sterile, e.g., for an injectable.

The term "pharmaceutically acceptable salts" refers to salts that are non-toxic in the amounts and concentrations at which they are administered. The preparation of such salts can facilitate pharmacological use by altering the physical characteristics of a compound (solubility) without preventing it from exerting its physiological effect.

The term "pharmaceutically acceptable composition" refers to a pharmaceutically active compound and one or more pharmaceutically acceptable carriers, excipients, and/or diluents.

The term "therapeutically effective amount" or "effective amount" is an amount of a preparation that alone, or together with further doses, produces the desired response. This may involve halting the progression of the disease or condition, delaying the onset of the disease or condition, or preventing the disease or condition from occurring, although it may also imply only temporarily slowing of the disease or condition.

The term "protein kinase-mediated disease or condition" refers to a disease or condition in which the biological function of a protein kinase affects the development, course, and/or symptoms of the disease or condition.

The term "mutants" refers to single or multiple amino acid changes in a protein as compared to the wild-type protein amino acid sequence.

Throughout the description and claims of this specification, the word "comprise" and variations of the word, such as "comprising" and "comprises," means "including but not limited to," and is not intended to exclude, for example, other additives, components, integers, or steps.

Compounds of the Invention

In one aspect, the present invention provides a compound having formula I:

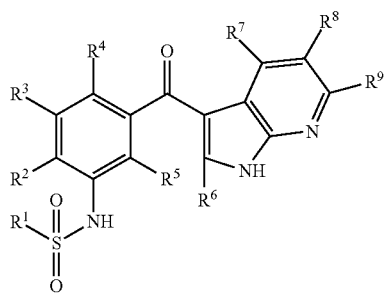

formula I all salts, prodrugs, tautomers and isomers thereof. In some embodiments of formula I, $R^1$ is a substituted lower alkyl or lower alkenyl, wherein the lower alkyl or lower alkenyl is substituted with one or more substituents selected from —OH, =O, and alkoxy; and $R^2$, $R^3$, $R^4$, $R^5$, $R^6$, $R^7$, $R^8$, and $R^9$ are independently selected from the group consisting of hydrogen, halogen, optionally substituted lower alkyl, optionally substituted lower alkenyl, optionally substituted cycloalkyl, optionally substituted heterocycloalkyl, optionally substituted aryl, optionally substituted heteroaryl, —CN, and —NO$_2$.

In one aspect, the present invention provides a compound having formula II:

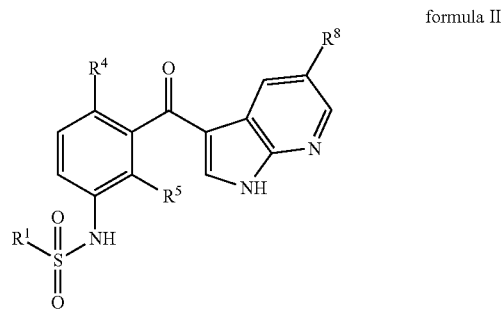

formula II all salts, prodrugs, tautomers and isomers thereof. In some embodiments of formula II, $R^1$ is a substituted lower alkyl or lower alkenyl, wherein the lower alkyl or lower alkenyl is substituted with one or more substituents selected from —OH, =O, and alkoxy; and $R^4$, $R^5$, and $R^8$ are independently selected from the group consisting of hydrogen, halogen, optionally substituted lower alkyl, optionally substituted lower alkenyl, optionally substituted cycloalkyl, optionally substituted heterocycloalkyl, optionally substituted aryl, optionally substituted heteroaryl, —CN, and —NO$_2$.

In one aspect, the present invention provides a compound having formula III:

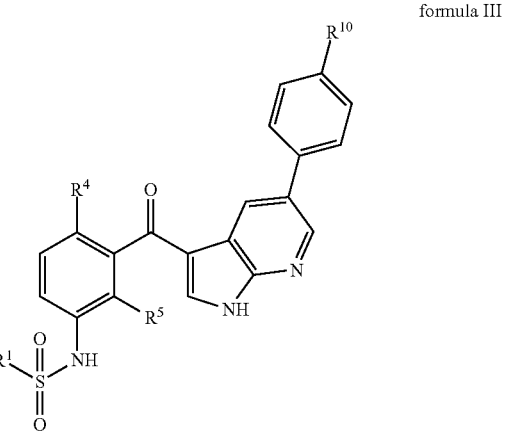

formula III all salts, prodrugs, tautomers and isomers thereof. In some embodiments of formula III, $R^1$ is a substituted lower alkyl or lower alkenyl, wherein the lower alkyl or lower alkenyl is substituted with one or more substituents selected from —OH, =O, and alkoxy; and $R^4$, $R^5$, and $R^{10}$ are independently selected from the group consisting of hydrogen, halogen, optionally substituted lower alkyl, optionally substituted lower alkenyl, optionally substituted cycloalkyl, optionally substituted heterocycloalkyl, optionally substituted aryl, optionally substituted heteroaryl, —CN, and —NO$_2$.

In one aspect, the present invention provides a compound having formula IV:

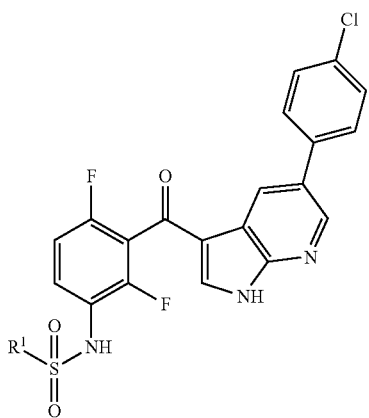

formula IV all salts, prodrugs, tautomers and isomers thereof. In some embodiments of formula III, R$^1$ is a substituted lower alkyl or lower alkenyl, wherein the lower alkyl or lower alkenyl is substituted with one or more substituents selected from —OH, =O, and alkoxy.

In one aspect, the present invention provides a compound having the structure of 200-17:

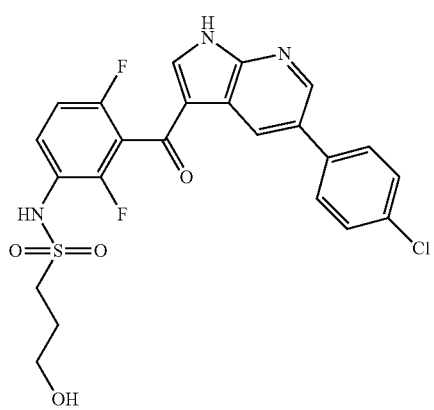

200-17 all salts, prodrugs, tautomers, and isomers thereof.

In another aspect, the present invention provides a compound having the structure of 200-73:

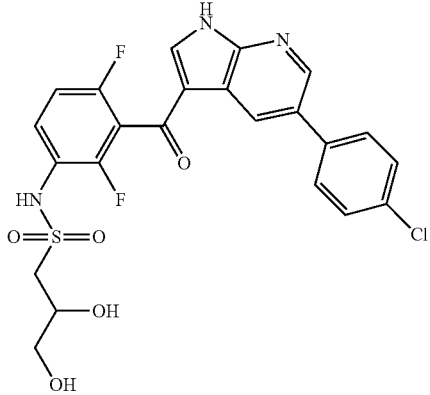

200-73 all salts, prodrugs, tautomers, and isomers thereof.

In another aspect, the present invention provides a compound having the structure of 200-93 and the resolved isomers 200-93a and 200-93b:

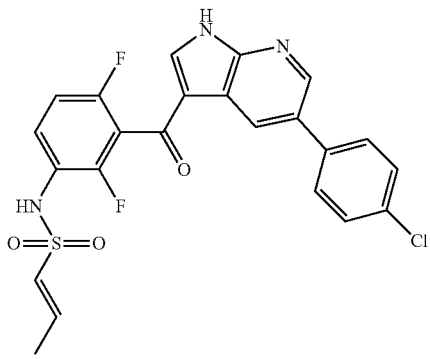

200-93 all salts, prodrugs, tautomers, and cis or trans isomers (200-93a and 200-93b) thereof.

In another aspect, the present invention provides compound having the structure of 200-115:

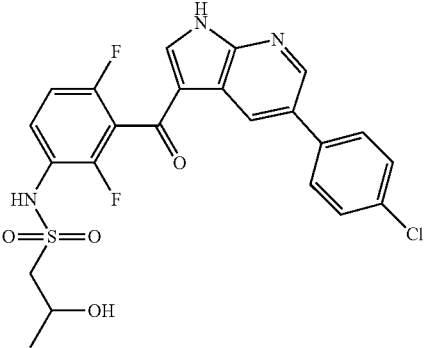

200-115 all salts, prodrugs, tautomers, and isomers thereof.

In another aspect, the present invention provides a compound having the structure of 200-117:

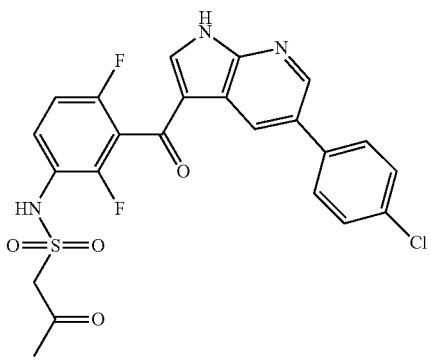

200-117 all salts, prodrugs, tautomers, and isomers thereof.

In another aspect, the present invention provides a compound having the structure of 200-123:

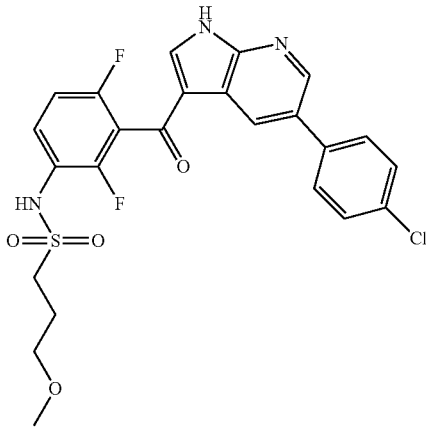

200-123 all salts, prodrugs, tautomers, and isomers thereof.

In another aspect, the present invention provides a compound having the structure of 200-139:

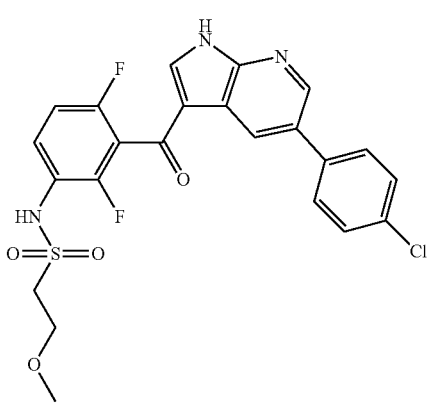

200-139 all salts, prodrugs, tautomers, and isomers thereof.

In another aspect, the present invention provides a compound having the structure of 200-149:

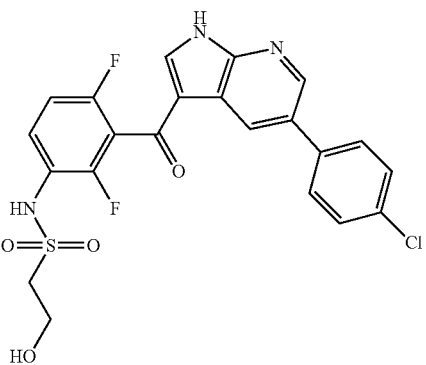

200-149 all salts, prodrugs, tautomers, and isomers thereof.

Protein Kinase Targets and Indications of the Invention

Protein kinases play key roles in propagating biochemical signals in diverse biological pathways. More than 500 kinases have been described, and specific kinases have been implicated in a wide range of diseases conditions. In one aspect, the invention provides methods for treating a protein kinase-mediated disease or condition in an animal or human subject, (i.e., indications) such as without limitation, cancer, cardiovascular disease, inflammatory disease, neurological disease, and other diseases. As such, kinases represent important control points for small molecule therapeutic intervention.

In another aspect, the invention provides a method for modulating the activity of a protein kinase selected from the group consisting of BRK, FGR, PDGFRα(V561D), DDR2, LYNa, SRM, PDGFRα, LCK, DDR1, KDR, ACK, JAK1, LYNb, KIT, CSK, YES, KIT(V560G), BLK, MST1, JAK2, RET(S891A), SRC, FYN(isoform a), RET(G691S), FYN (isoform b), PDGFRβ, RET, FLT4, RET(Y791F), skMLCK, FRK, MST2, FLT1, AurA, FLT3, JAK3, RET(M918T), WNK3, p38β, FGFR2, MNK1, MNK2, PIK3CA/PIK3R1, PDGFRα(D842V), MET, FGFR1, BRAF(V600E), MAP2K5, KIT(D816E), ALK, FGFR3, RAF1, MAP2K3, HER4, KIT(D816V), Erk5, EGFR, YES(T348I), KIT (V654A), KIT(D816Y), PDGFRα(T674I), BRAF, ABL, HER2, EPHA5, ROCK2, KIT(T670I), PKD3, MST4, MAP2K1, MAP2K2, MST3, ROCK1, IGF1R, PKD2, MAP2K6, Erk2, PKD1, MAP2K7, Erk1, MAP2K4, and BTK by contacting the protein kinase with an effective amount of a compound of formulas I, II, III, IV, 200-17, 200-73, 200-93, 200-93a, 200-93b, 200-115, 200-117, 200-123, 200-139 or 200-149.

In another aspect, the invention provides a method for treating a protein kinase-mediated disease or condition in an animal subject, wherein the method involves administering to the subject an effective amount of a composition including a compound of formulas I, II, III, IV, 200-17, 200-73, 200-93, 200-93a, 200-93b, 200-115, 200-117, 200-123, 200-139 or 200-149.

In one aspect, the invention provides a method for treating a disease or condition, mediated by a protein kinase selected from the group consisting of BRK, FGR, PDGFRα(V561D), DDR2, LYNa, SRM, PDGFRα, LCK, DDR1, KDR, ACK, JAK1, LYNb, KIT, CSK, YES, KIT(V560G), BLK, MST1, JAK2, RET(5891A), SRC, FYN(isoform a), RET(G691S), FYN(isoform b), PDGFRβ, RET, FLT4, RET(Y791F), skM- LCK, FRK, MST2, FLT1, AurA, FLT3, JAK3, RET (M918T), WNK3, p38β, FGFR2, MNK1, MNK2, PIK3CA/PIK3R1 PDGFRα(D842V), MET, FGFR1, BRAF(V600E), MAP2K5, KIT(D816E), ALK, FGFR3, RAF1, MAP2K3, HER4, KIT(D816V), Erk5, EGFR, YES(T348I), KIT (V654A), KIT(D816Y), PDGFRα(T674I), BRAF, ABL, HER2, EPHA5, ROCK2, KIT(T670I), PKD3, MST4, MAP2K1, MAP2K2, MST3, ROCK1, IGF1R, PKD2, MAP2K6, Erk2, PKD1, MAP2K7, Erk1, MAP2K4, and BTK by contacting the protein kinase with an effective amount of a compound of formulas I, II, III, or IV, 200-17, 200-73, 200-93, 200-93a, 200-93b, 200-115, 200-117, 200-123, 200-139 or 200-149.

A number of different assays for kinase activity can be utilized for assaying for active modulators and/or determining specificity of a modulator for a particular kinase or group of kinases. In addition to the assay mentioned in the Examples below, one of ordinary skill in the art will know of other assays that can be utilized or can be modified for a particular application.

In a commonly used in vitro screen used to measure inhibition of battery of selected protein kinases (see Example 9) including BRK, FGR, PDGFRα(V561D), DDR2, LYNa, SRM, PDGFRα, LCK, DDR1, KDR, ACK, JAK1, LYNb, KIT, CSK, YES, KIT(V560G), BLK, MST1, JAK2, RET(S891A), SRC, FYN(isoform a), RET(G691S), FYN(isoform b), PDGFRβ, RET, FLT4, RET(Y791F), skM-LCK, FRK, MST2, FLT1, AurA, FLT3, JAK3, RET (M918T), WNK3, p38β, FGFR2, MNK1, MNK2, PIK3CA/PIK3R1, PDGFRα(D842V), MET, FGFR1, BRAF(V600E), MAP2K5, KIT(D816E), ALK, FGFR3, RAF1, MAP2K3, HER4, KIT(D816V), Erk5, EGFR, YES(T348I), KIT (V654A), KIT(D816Y), PDGFRα(T674I), BRAF, ABL, HER2, EPHA5, ROCK2, KIT(T670I), PKD3, MST4, MAP2K1, MAP2K2, MST3, ROCK1, IGF1R, PKD2, MAP2K6, Erk2, PKD1, MAP2K7, Erk1, MAP2K4, and BTK, compounds 200-17, 200-73, 200-93a, 200-93b, 200-115, 200-117, 200-123, and 200-139 were found to display activity to inhibit BRK, SRM, FOR, LCK, KIT, and JAK1, among others (see Tables 1 and 2).

In one aspect, compounds 200-17, 200-73, 200-93a, 200-93b, 200-115, 200-117, 200-123, and 200-139 displayed low nM activity to greater than 30% inhibition of Breast tumor related kinase (BRK), or protein tyrosine kinase 6 (PTK6) BRK. As described below, inhibition of BRK is an important target for a cancer therapy, particularly breast cancer, as BRK participates in both cell dysregulation and metastasis. BRK inhibition may offer a therapeutic approach for treating patients with Her2 targeted therapy-resistant breast cancers and patients with ERBB2/HER2-positive breast cancers (see below).

As a further test of biological activity, compounds were assayed for inhibition of cell growth using the breast cancer cell line T-47D (see Example 10). In this cell based assay, the $IC_{50}$ values for 200-17, 200-73, 200-93b, 200-115, 200-117, 200-123, 200-139 and 200-149 were less than 20 µM, while the $IC_{50}$ value for 200-93a was greater than 20 µM.

Protein kinase targets for compounds of formula I, II, III and IV, 200-17, 200-73, 200-93, 200-93a, 200-93b, 200-115, 200-117, 200-123, 200-139 and 200-149 include the following: ALK, B-Raf, C-Raf-1, EGFR, Erk2, FGFR, Frk, Fyn, HCK, Her2/Erbb2, Her4/Erbb4, Jak1, Jak2, Jak 3, Kdr, Kit, LCK, MAP2K1, MAP2K2, MAPKAPK2, PDGFR, PDGFRα, PDGFRβ, Ret, Src, TNF-Related Activation-Induced Cytokine (TRANCE), Stk6, Aurora A, Aurora B, Aurora C, and Yes (See U.S. Pat. No. 8,470,818 B2 for detailed information about the above listed kinases).

Breast tumor related kinase (BRK), or protein tyrosine kinase 6 (PTK6) is a non-receptor type tyrosine kinase, cloned from a metastatic breast tumor, and overexpressed in a majority of breast cancers (Mizuguchi id.; Ono, H. et al. PTK6 Promotes Cancer Migration and Invasion in Pancreatic Cancer Cells Dependent on ERK Signaling. 2014, PLoS ONE 9(5): e96060. doi:10.1371/journal.pone.0096060). BRK is composed of an amino-terminal SH3 domain, SH2 domain, and carboxyl-terminal kinase domain (Park, S. H. et al. PTK6 Inhibition Promotes Apoptosis of Lapatinib-Resistant Her2+ Breast Cancer Cells by Inducing Bim, Breast Cancer Research 2015, 17: 86, doi 10.1186/s13058-015-0594-z). BRK is expressed in many human cancers including breast, ovary, colon head and neck squamous cell carcinoma, prostate, lung, bladder, pancreas, and gastric, and lymphomas (Mizuguchi id.). BRK is only weakly expressed in normal mammary tissue or benign lesions (Mizuguchi id.). BRK has been shown to be activated downstream of various receptors in response to stimulation by their respective ligands such as EGF, HGF, and IGF (Goel, R. K. et al. Tracing the Footprints of the Breast Cancer Oncogene BRK—Past Till Present, Biochemica et Biophysics Acta 2015, 1656:39-54). Since the signaling pathways activated by these ligands tend to promote cell proliferation and migration, activation of BRK downstream in these signaling pathways is predicated to mechanistically contribute to the promotion of oncogenesis (Goal id.). Although the physiological function of BRK is dependent on its activation status, level of expression, intracellular localization, interaction with various signaling intermediates, and tumor stage or grade, ample evidence suggests that targeting BRK should provide therapeutic benefits in treating breast cancer (Goel id.). The oncogenic functions of BRK are reported to be mediated via its kinase activity, thus the development of clinical inhibitors of the BRK kinase domain should be an attractive therapeutic target (Goal id.).

In breast cancer, a 20-30% incidence of over expression of the epidermal growth factor receptor family tyrosine kinase ERBB2 (HER2, Neu) has been reported (Peng, M et al. Protein Tyrosine Kinase 6 Promotes ERBB2-induced Mammary Gland Tumorigenesis in the Mouse. Cell Death and Disease. 2015, 6:e1848; published online 6 Aug. 2015). Furthermore BRK expression, activation, and amplification of the BRK gene have been reported to occur in ERBB2/HER2-positive mammary gland cancers (Peng id.). The role of BRK (PTK6) to promote mammary gland tumorigenesis by activated ERBB2 was explored by Peng and co-workers using transgenic mice prepared by crossing PTK6 −/− mice with a mouse mammary tumor virus-ERBB2 transgenic mouse line expressing activated ERBB2. In mice lacking BRK, ERBB2-induced tumorigenesis was significantly delayed and diminished. BRK expression was induced in the mammary glands of ERBB2 transgenic mice before tumor development and correlated with activation of signal transducer and activator of transcription 3 (STAT3) and increased proliferation. Disruption of BRK-impaired STAT3 activation and proliferation. Additionally, phosphorylation of the BRK substrates focal adhesion kinase (FAK) and breast cancer anti-estrogen resistance 1 (BCAR1; p130CAS) were decreased in BRK −/− mammary gland tumors. Reduced numbers of metastases were detected in the lungs of BRK −/− mice expressing activated ERBB2, compared with wild-type ERBB2 transgenic mice. These data support roles for BRK in both ERBB2-induced mammary gland tumor initiation and metastasis, and identify STAT3, FAK, and BCAR1 as physiologically relevant BRK substrates in breast cancer. This led the authors to conclude that including BRK inhibitors as part of a treatment regimen could have distinct benefits in ERBB2/HER2-positive breast cancers.

BRK is highly expressed in Human Epidermal Growth Factor 2+ (Her2+) breast cancers (Park id.). Park and co-workers investigated whether BRK inhibition is an effective strategy to inhibit growth and survival of Her2+ breast cancer cells, including those that are relatively resistant to Lapatinib, a targeted therapy for Her2+ breast cancer that developed either intrinsically or was acquired after continuous drug exposure. The authors reported that BRK down-regulation induces apoptosis of Lapatinib-resistant Her2(+) breast cancer cells by enhancing Bim, a pro-apoptotic Bcl2 family member expressed via p38 activation. As Bim expression is a critical biomarker for response to many targeted therapies, BRK inhibition may offer a therapeutic approach to treating patients with Her2 targeted therapy-resistant breast cancers.

Recently, Mahmoud and co-workers reported the discovery of derivatives of pyrido[2,3-b]indole derivatives with 4-anilne and 6-substitutions as potent inhibitors of BRK and/or Her2 and described structure activity relationships (Mahmoud, K. A. Novel Inhibitors of Breast Cancer Relevant Kinases BRK and Her2. Med. Chem. Commun. 2014, 5:659-664). In a docking model developed by these researchers, the ATP-binding pocket in BRK was found to favor hydrophilic substituents. Mahmoud and co-workers further disclose a series of 4-anilinoa α-carbolines as novel Brk Inhibitors (Mahmoud, K. Z. et al. "Discovery of 4-Anilino α-Carbolines s Novel Brk inhibitors" Bioorganic and Medicinal Chemistry Letters 2014, 24: 1948-1951). In conclusion, the presented series of 4-anilino α-carbolines turned out as a highly promising class of anticancer agents. The Brk inhibition depends on the kind and positioning of the aniline substituents which lead to nanomolar as well as to inactive inhibitors. The observed protein kinase inhibition profile documented a first selectivity of Brk inhibition. The correlation of Brk inhibition and mediated antiproliferative activity better than that of the reported lapatinib qualifies the new compound class for further preclinical studies (Mahmoud 2014 id.), Zeng et at disclose a group of novel imidazol [1,2a] pyrazin-8 amines as potent inhibitors of BRK and a computational model for inhibition of BRK (Zing, H. et at "Discovery of Novel Imidazo [1,2-a] Pyrazin-8-Amines as Brk/PTK6 inhibitors" Bioorganic and Medicinal Chemistry Letters 2011, 21: 5870-5876). In addition, Several inhibitors, with single-digit nanomolar target engagement cell-based activity and an appealing overall DMPK profile, could be used as tool compounds to further validate Brk/PTK6 as a potential target for cancer treatment. None of these compounds have the chemical structure of formulas I, II, III, or IV, 200-17, 200-73, 200-93, 200-93a, 200-93b, 200-115, 200-117, 200-123, 200-139, or 200-149.

Ren, P. et al. disclose a series of compounds and compositions as protein kinase inhibitors including BRK inhibitors (US 2010/0048552 A1). The novel compounds inhibit one or more protein kinases and are, therefore, expected to be useful in treatment of kinase-mediated diseases or conditions. None of these compounds have the chemical structure of formulas I, II, III, or IV, 200-17, 200-73, 200-93, 200-93a, 200-93b, 200-115, 200-117, 200-123, 200-139, or 200-149.

In one aspect, compounds of formulas I, II, III, or IV, 200-17, 200-73, 200-93, 200-93a, 200-93b, 200-115, 200-117, 200-123, 200-139 or 200-149 including salts, prodrugs, and/or isomers thereof, can be used in preparation of medicaments for the treatment of a BRK-mediated disease or condition. In particular the disease or condition is cancer. The types of cancers include breast, ovary and colon, and head and neck squamous cell carcinoma. In particular, the disease or condition is breast cancer including ERBB2/HER2-positive breast cancer and Her2 targeted therapy-resistant breast cancer.

The amounts of compounds of formulas I, II, III, or IV, 200-17, 200-73, 200-93, 200-93a, 200-93b, 200-115, 200-117, 200-123, 200-139 or 200-149 to be administered can be determined by standard procedures taking into account factors such as the compounds $IC_{50}$; the biological half-life of the compound; the age, size, and weight of the subject; and the condition associated with the subject. In general, routine experimentation in clinical trials will determine specific ranges for optimal therapeutic effect for each therapeutic agent and each administrative protocol and administration to specific patients will be adjusted to within effective and safe ranges depending on the patient's condition and responsiveness to initial administration. However, the ultimate administration protocol will be regulated according to the judgment of the attending clinician considering such factors as age, gender, condition, and size of the patient. Generally, doses of active compounds may range from about 0.01 mg/kg per day to, about 1000 mg/kg per day. Compounds described herein can be administered in single or multiple doses.

Combination Therapy

In one aspect, the composition to be administered can include a plurality of different pharmacologically active compounds which can include a plurality of compounds of the invention including compounds of formulas I, II, III, and IV, 200-17, 200-73, 200-93, 200-93a, 200-93b, 200-115, 200-117, 200-123, 200-139 and 200-149. Compounds of formulas I, II, III, and IV, 200-17, 200-73, 200-93, 200-93a, 200-93b, 200-115, 200-17, 200-200-123, 200-139 and 200-149 that are therapeutically effective for the same protein kinase-mediated disease or condition, wherein the compounds have an additive or a synergistic effect on the disease indication, may be found to be effective.

In one aspect, the invention provides methods for treating a BRK-mediated disease or condition in an animal or human subject, wherein the method involves administering to the subject an effective amount of a compound of formulas I, II, III, or IV, 200-17, 200-73, 200-93, 200-93a, 200-93b, 200-115, 200-117, 200-200-123, 200-139 or 200-149, in combination with one or more other therapies for treating the same disease or condition. Other therapies include medical procedures (such as surgeries), therapeutics, and/or radiation. Combination therapy can include administration of the compounds described herein with one or more other therapeutics at different times, or co-administration of the compounds described herein with one or more other therapeutics. In some embodiments, dosages may be modified for one, or more of the compounds of the invention or other therapeutics used in combination, such modifications being a reduction in the dose amounts relative to a compound or therapy used alone.

It is understood that use in combination includes use with other medical procedures, therapeutics, and therapies where the other therapy or drug may be administered at different times, within a short time period, such as within 1, 2, 3, or 4-24 hours, or within a longer time period, such a 1-2 days, 2-4 days, 4-7 days, or 1-4 weeks. Use of the compounds of the invention can be in combination with a medical procedure such as surgery, performed on the subject once or infrequently, where the compounds are administered within a short time or longer time before or after the medical procedure.

Administration

The methods and compounds will typically be used in therapy for human subjects with a kinase-mediated disease or condition. However, they may also be used to treat similar or identical indications in other animal subjects. In this context, the terms "subject," "animal subject," and the like refer to human and non-human vertebrates, i.e., mammals, such as non-human primates, sports and commercial animals, e.g., equines, bovines, porcines, ovines, rodents, and pets, e.g. canines and felines.

In another aspect, the compounds of formulas I, II, III, or IV, 200-17, 200-73, 200-93, 200-93a, 200-93b, 200-115, 200-117, 200-200-123, 200-139 or 200-149 may be administered intravenously, intramuscularly, subcutaneously, orally, transdermally, transmucosal, rectally, or by inhalation. In the case of intravenous administration, the dose may be administered as a bolus or infusion.

Pharmaceutical preparations for oral use can be obtained, for example, by combining the compounds of formulas I, II, III, or IV, 200-17, 200-73, 200-93, 200-93a, 200-93b, 200-115, 200-117, 200-200-123, 200-139 or 200-149 with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

For injection, the compounds of formulas I, II, III, or IV, 200-17, 200-73, 200-93, 200-93a, 200-93b, 200-115, 200-117, 200-200-123, 200-139 or 200-149 are formulated in sterile liquid solutions, preferably in physically compatible buffers or solutions, such as saline solution, Hank's solution, or Ringer's solution. In addition, the compounds may be formulated in solid form and re-dissolved or suspended immediately prior to use. Lyophilized forms can also be produced.

The administration of the compounds described herein can occur simultaneously or sequentially with chemotherapy or radiation. It is understood that administration of other therapeutics or drugs to treat a medical disease or condition can be by a different route of administration or by the same route of administration.

In another aspect, the use in combination therapy for any route of administration includes delivery of compounds of the invention and one or more other drug therapeutics delivered by the same route of administration together in any formulation, or administered together, within an hour, 2 hours, 3 hours, up to 24 hours, in separate formulations or by different routes of administration.

The invention also provides for a pharmaceutical combination, e.g., a kit, comprising (a) a first agent which is a compound of the invention as disclosed herein, in free form or in pharmaceutically acceptable salt form, and (b) at least one co-agent. The kit can include instructions for its administration.

General Synthetic Methods

The present invention also includes processes for the preparation of compounds of the invention. In the reactions described, it can be necessary to protect reactive functional groups, for example hydroxy, amino, imino, thio, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry," John Wiley and Sons, 1991. Detailed examples for the synthesis of compounds 200-17, 200-73, 200-93 (resolution of isomers), 200-115, 200-117, 200-123, 200-139, and 200-149 can be found in the Examples.

Synthesis of 200-17: Compound 200-17 is synthesized using the method shown in Scheme 1 starting with commercially available 2,6-difluoro-3-nitrobenzoic acid (1) and converting it into the corresponding acyl chloride (2). To a mixture of 5-bromo-7-azaindole in 1,2-dichloroethane is added a Lewis Acid (i.e., aluminum chloride) followed by addition of the acyl chloride (2) to produce (5-bromo-1H-pyrrolo[2,3-b]pyridine-3-yl)-2,6-difluoro-3-nitrophenyl) methanone (3). The nitrophenyl group of intermediate (3) is reduced to form (3-amino-2,6-difluoro-phenyl)-(5-bromo-1H-pyrrolo[2,3-b]pyridin-3-yl)methanone (4) which is reacted under anhydrous conditions with 2,6-dichlorodbenzoyl chloride in the presence of triethylamine and 4-dimethylaminopyridine to produce (3-amino-2,6-difluoro-phenyl)-[5-bromo-1-(2,6-dichlorobenzoyl)pyrrolo [2,3-b] pyridin-3-yl] methanone (5). The intermediate (5) is reacted with 4-chlorobenzeneboronic acid and palladium dichloride to produce (3-amino-2,6-difluorophenyl)-[5-(4-chlorophenyl)-1-(2,6-dichlorobenzoyl)pyrrolo [2,3-b] pyridin-3-yl] methanone (6). The intermediate (6) is reacted with 3-(acetyloxy)-1-propanesulfonyl chloride to form N-[3-[5-(4-chlorophenyl)-1-(2,6-dichlorobenzoyl)pyrrolo[2,3-b] pyridine-3-carbonyl]-2,4-difluoro-phenyl] 3-(acetyloxy) propane-1-sulfonamide (7). The intermediate (7) is deprotected, removal of the dichlorobenzoyl group, using standard conditions to produce 200-17.

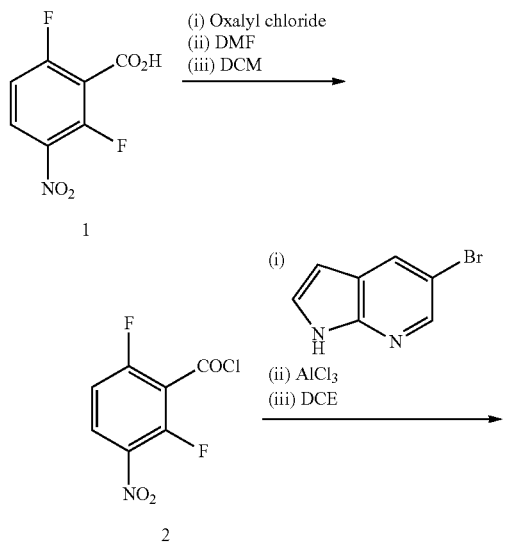

Scheme 1
Synthesis of 200-17

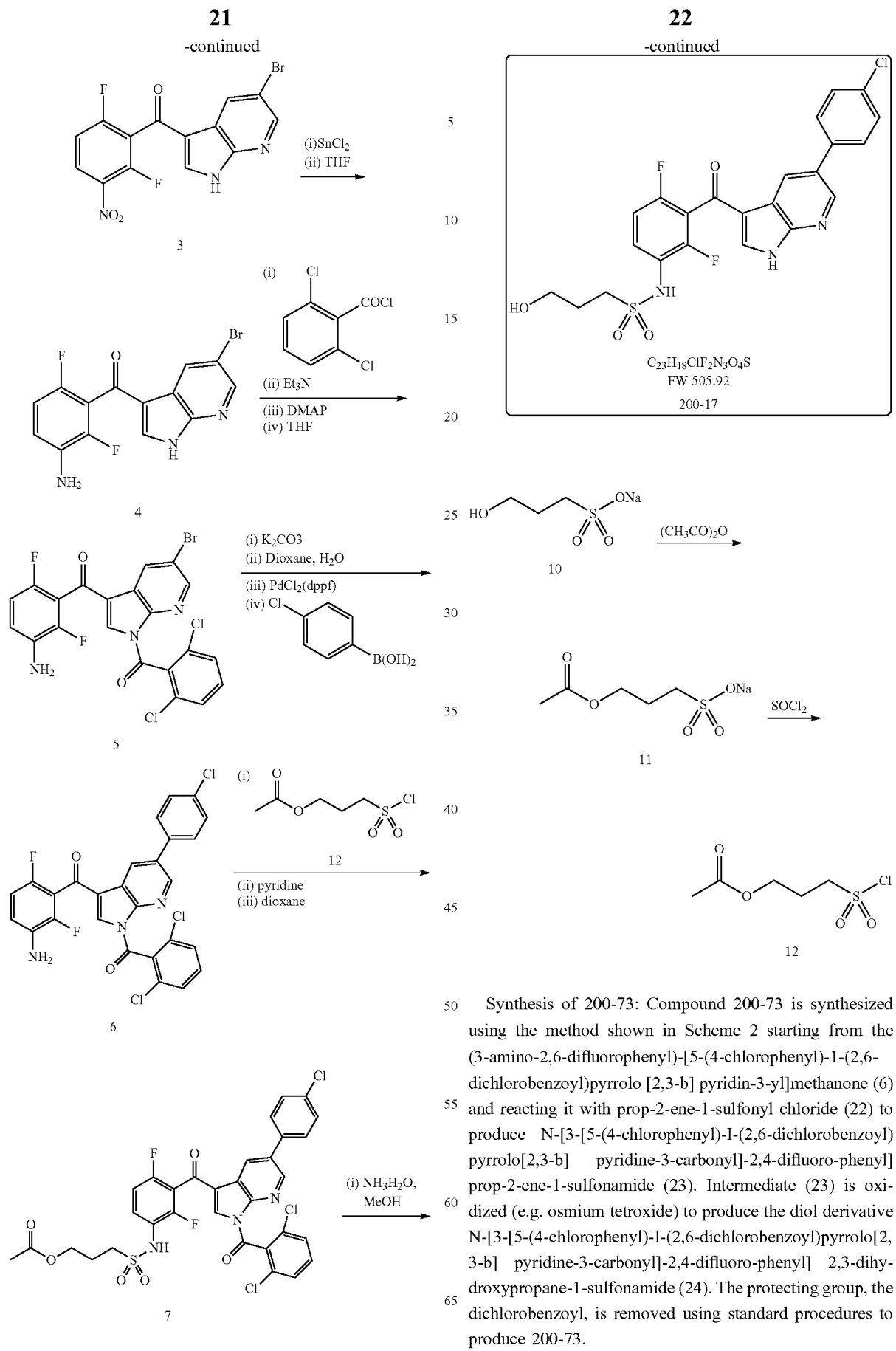

Synthesis of 200-73: Compound 200-73 is synthesized using the method shown in Scheme 2 starting from the (3-amino-2,6-difluorophenyl)-[5-(4-chlorophenyl)-1-(2,6-dichlorobenzoyl)pyrrolo [2,3-b] pyridin-3-yl]methanone (6) and reacting it with prop-2-ene-1-sulfonyl chloride (22) to produce N-[3-[5-(4-chlorophenyl)-I-(2,6-dichlorobenzoyl) pyrrolo[2,3-b] pyridine-3-carbonyl]-2,4-difluoro-phenyl] prop-2-ene-1-sulfonamide (23). Intermediate (23) is oxidized (e.g. osmium tetroxide) to produce the diol derivative N-[3-[5-(4-chlorophenyl)-I-(2,6-dichlorobenzoyl)pyrrolo[2,3-b] pyridine-3-carbonyl]-2,4-difluoro-phenyl] 2,3-dihydroxypropane-1-sulfonamide (24). The protecting group, the dichlorobenzoyl, is removed using standard procedures to produce 200-73.

Scheme 2
Synthesis of 200-73

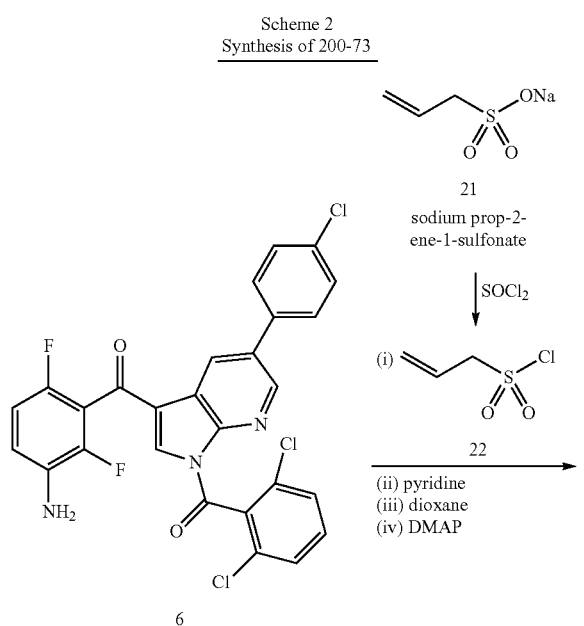

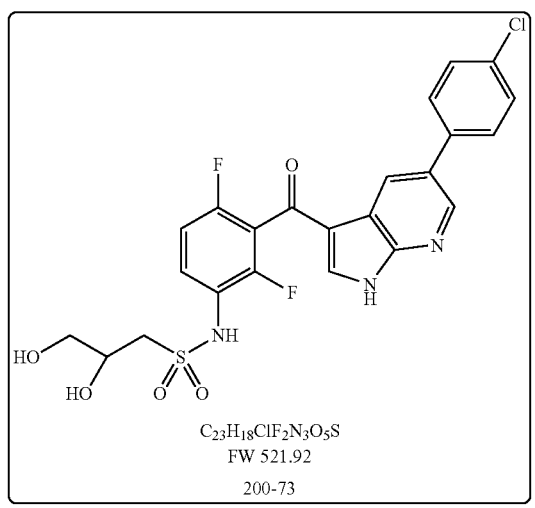 [SMILES: O=C(c1c(F)ccc(NS(=O)(=O)CC(O)CO)c1F)c1c[nH]c2ncc(-c3ccc(Cl)cc3)cc12]

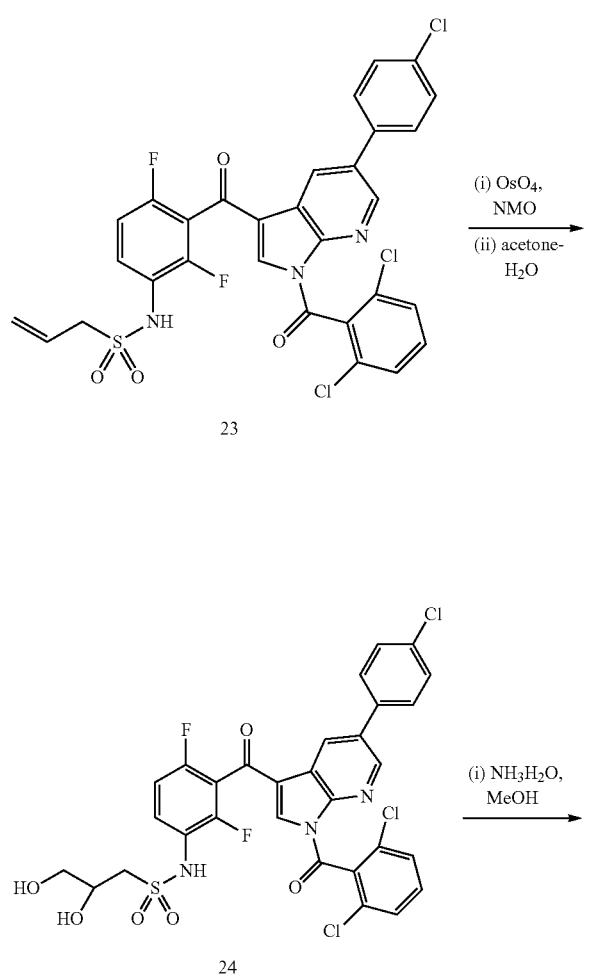

Synthesis of 200-93: Compound 200-93 is synthesized using the method described in Scheme 3 starting from (3-amino-2,6-difluorophenyl)-[5-(4-chlorophenyl)-1-(2,6-dichlorobenzoyl)pyrrolo[2,3-b] pyridin-3-yl]methanone (6) and reacting it with 2-(benzyloxy)-1-propanesulfonyl chloride (35) in dioxane containing pyridine and 4-dimethylaminopyridine to produce N-[3-[5-(4-chlorophenyl)-I-(2,6-dichlorobenzoyl)pyrrolo[2,3-b] pyridine-3-carbonyl]-2,4-difluoro-phenyl]prop-1-ene-1-sulfonamide (36). The intermediate (36) is deprotected, removal of the dichlorobenzoyl group, using standard conditions to produce 200-93 as a mixture of (cis) and (trans) isomers. The two isomers are resolved by HPLC, and named 200-93a and 200-93b, respectively.

Scheme 3
Synthesis of 200-93

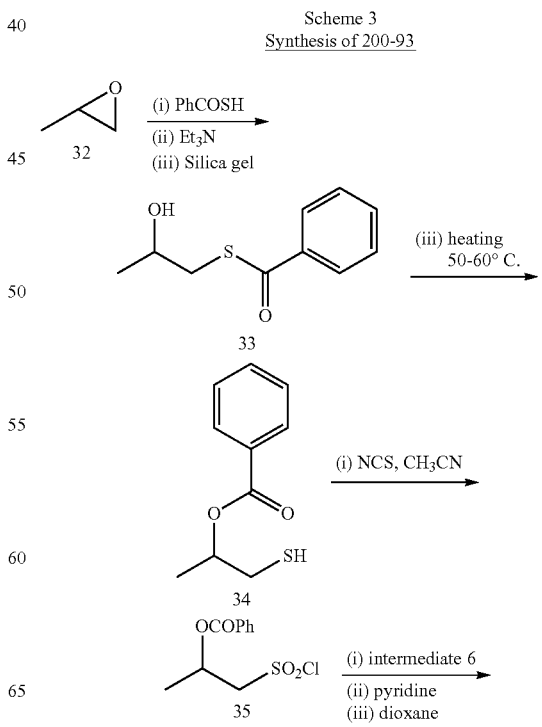

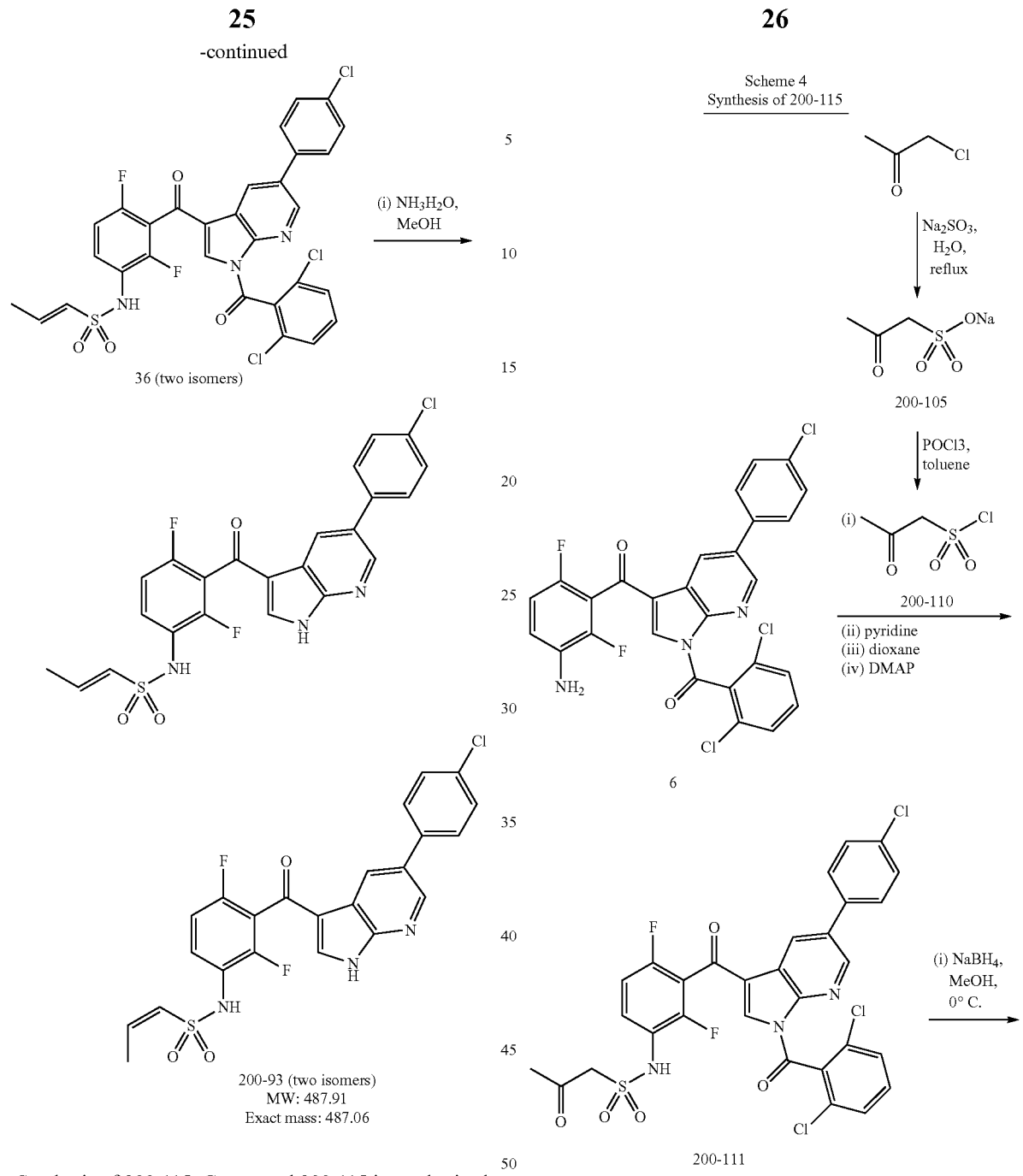

Synthesis of 200-115: Compound 200-115 is synthesized using the method shown in Scheme 4 starting from (3-amino-2,6-difluorophenyl)-[5-(4-chlorophenyl)-1-(2,6-dichlorobenzoyl)pyrrolo [2,3-b] pyridin-3-yl]methanone (6) and reacting it with 2-oxopropanesulfonyl chloride, to produce N-[3-[5-(4-chlorophenyl)-I-(2,6-dichlorobenzoyl)pyrrolo[2,3-b] pyridine-3-carbonyl]-2,4-difluoro-phenyl]-2-oxopropane-1-sulfonamide (200-111). The intermediate (200-111) is treated sodium borohydride to reduce the ketone to the alcohol and produce N-[3-[5-(4-chlorophenyl)-I-(2,6-dichlorobenzoyl)pyrrolo[2,3-b] pyridine-3-carbonyl]-2,4-difluoro-phenyl]-2-hydroxypropane-1-sulfonamide (200-113). The alcohol (200-113) is deprotected by removal of the dichlorobenzoyl group, using standard conditions to produce 200-115 consisting of a mixture of R and S isomers.

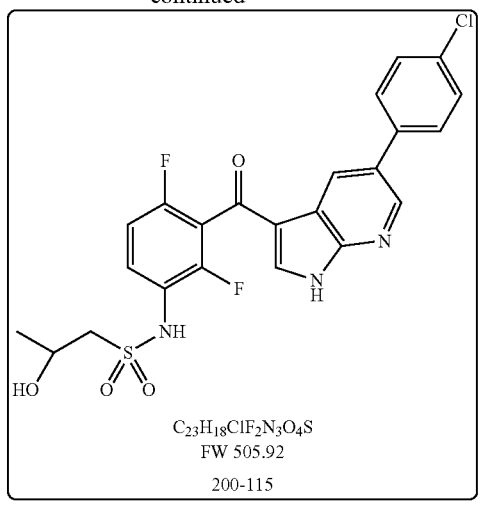

C₂₃H₁₈ClF₂N₃O₄S
FW 505.92
200-115

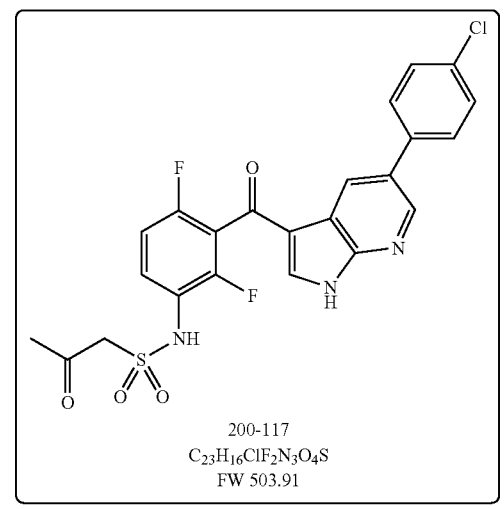

200-117
C₂₃H₁₆ClF₂N₃O₄S
FW 503.91

Synthesis of 200-117: Compound 200-117 is synthesized using the method shown in Scheme 5 starting from N-[3-[5-(4-chlorophenyl)-1-(2,6-dichlorobenzoyl)pyrrolo[2,3-b]pyridine-3-carbonyl]-2,4-difluoro-phenyl]-2-oxopropane-1-sulfonamide (200-111). The protecting dichlorobenzoyl group is removed using standard conditions to produce 200-117.

Scheme 5
Synthesis of 200-117

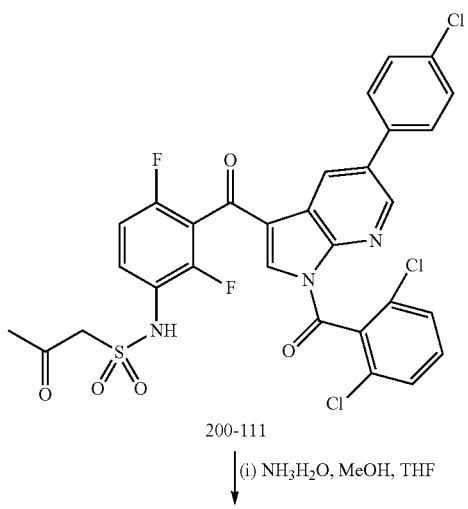

200-111

(i) NH₃H₂O, MeOH, THF

Synthesis of 200-123: Compound 200-123 is synthesized using the method shown in Scheme 6 starting from 3-amino-2,6-difluorophenyl)-[5-(4-chlorophenyl)-1-(2,6-dichlorobenzoyl)pyrrolo [2,3-b] pyridin-3-yl]methanone (6) [see Scheme 1] and reacting it with 3-methoxypropane-1-sulfonyl chloride (200-120) in dioxane containing pyridine and 4-dimethylaminopyridine to produce N-[3-[5-(4-chlorophenyl)-I-(2,6-dichlorobenzoyl)pyrrolo[2,3-b] pyridine-3-carbonyl]-2,4-difluoro-phenyl]-3-methoxypropane-1-sulfonamide (200-121). The protecting dichlorobenzoyl group is removed using standard conditions to produce 200-123.

Scheme 6
Synthesis of 200-123

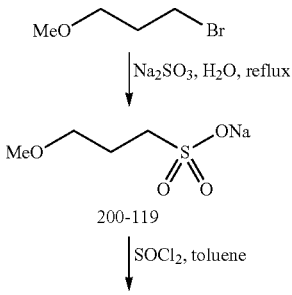

200-119

SOCl₂, toluene

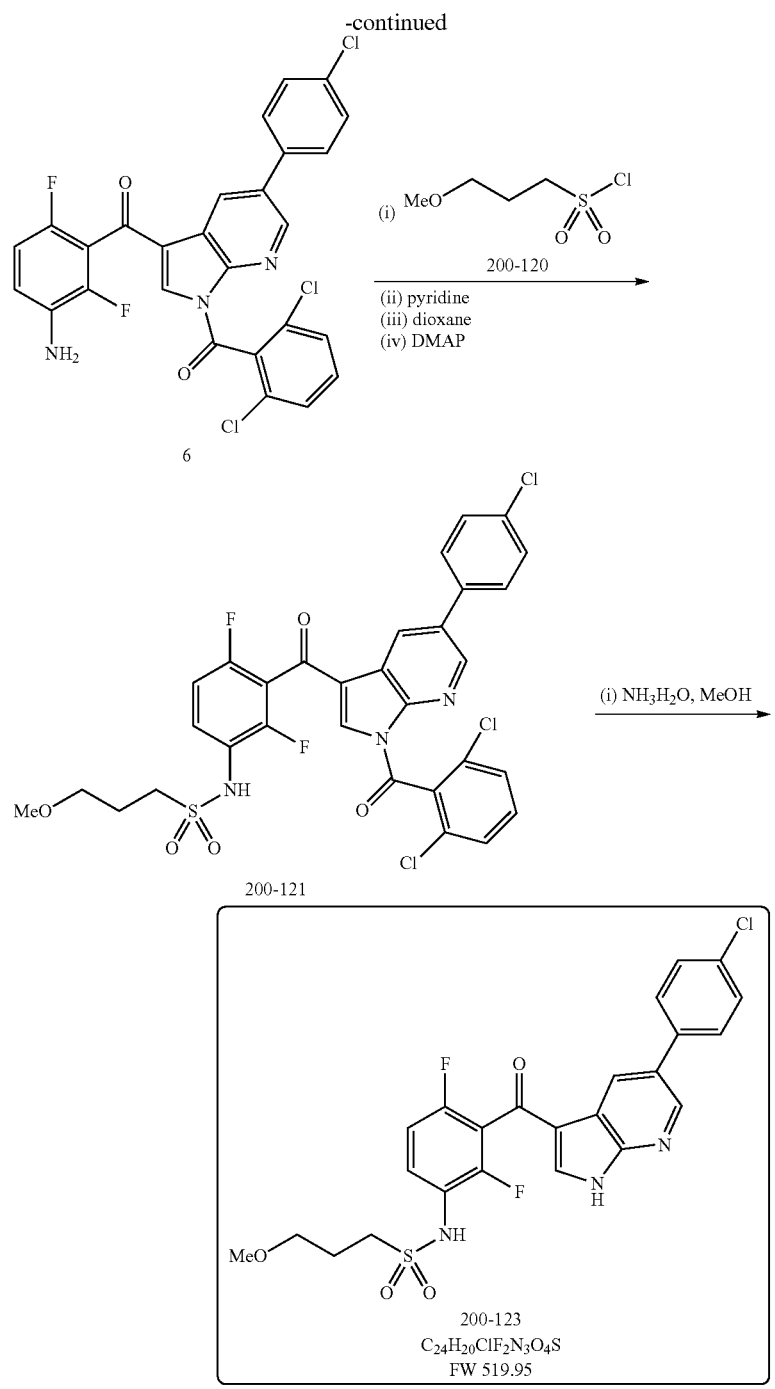

Synthesis of 200-129: Compound 200-139 is synthesized using the method shown in Scheme 7 starting from 3-amino-2,6-difluorophenyl)-[5-(4-chlorophenyl)-1-(2,6-dichlorobenzoyl)pyrrolo [2,3-b] pyridin-3-yl]methanone (6) [see Scheme 1] and reacting it with 2-methoxyethanesulfonyl chloride (200-136) in dioxane containing pyridine and 4-dimethylaminopyridine to produce N-[3-[5-(4-chlorophenyl)-1-(2,6-dichlorobenzoyl)pyrrolo[2,3-b] pyridine-3-carbonyl]-2,4-difluorophenyl]-2-methoxyethanesulfonamide (200-137). The protecting dichlorobenzoyl group is removed using standard conditions to produce 200-139.

Scheme 7
Synthesis of 200-139

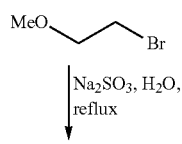

-continued

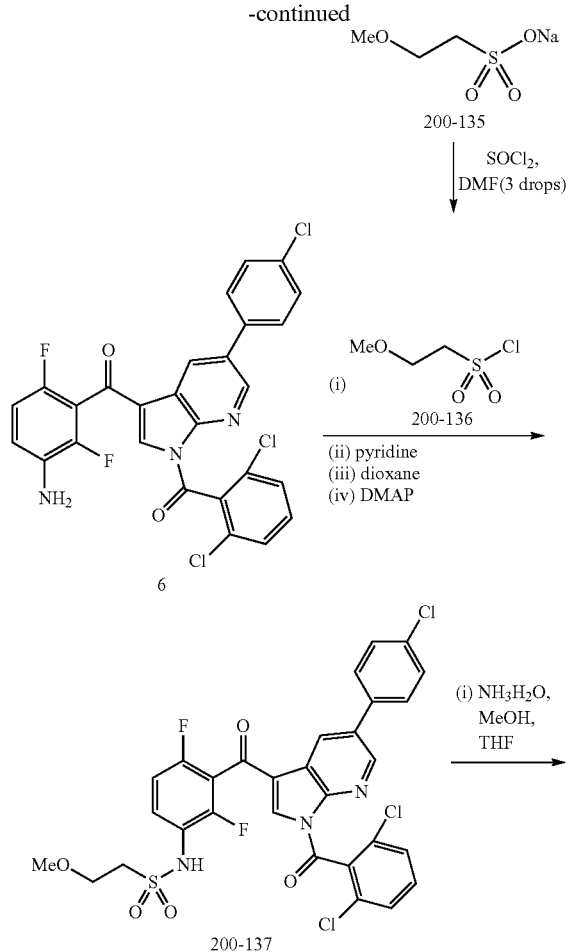

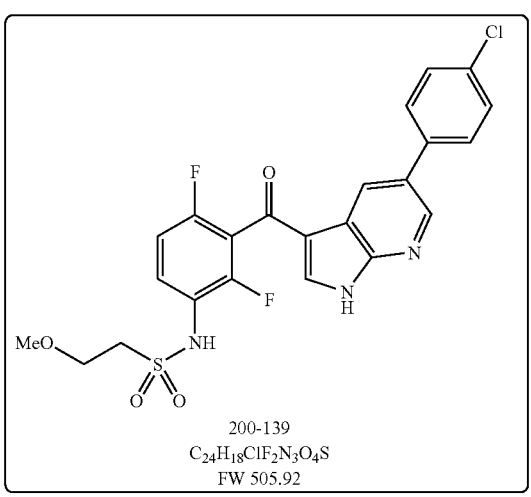

200-139
C$_{24}$H$_{18}$ClF$_2$N$_3$O$_4$S
FW 505.92

Scheme 8
Synthesis of 200-149

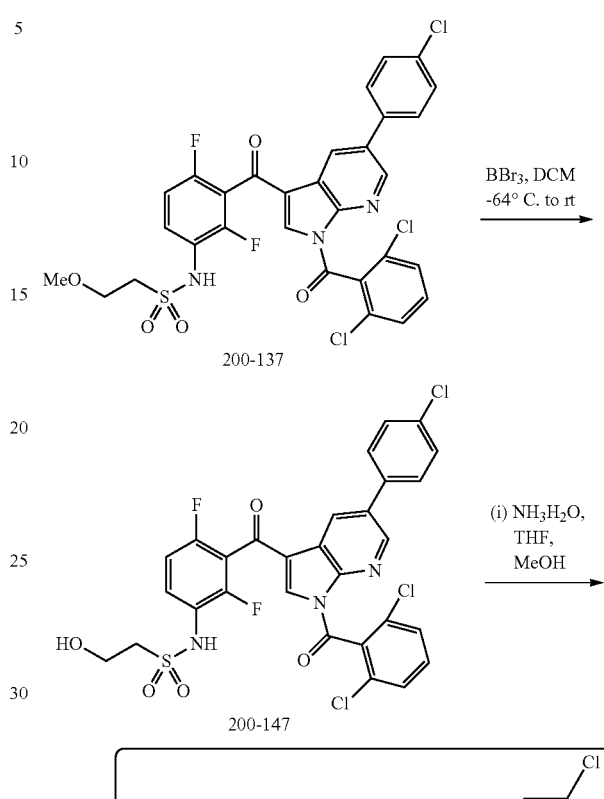

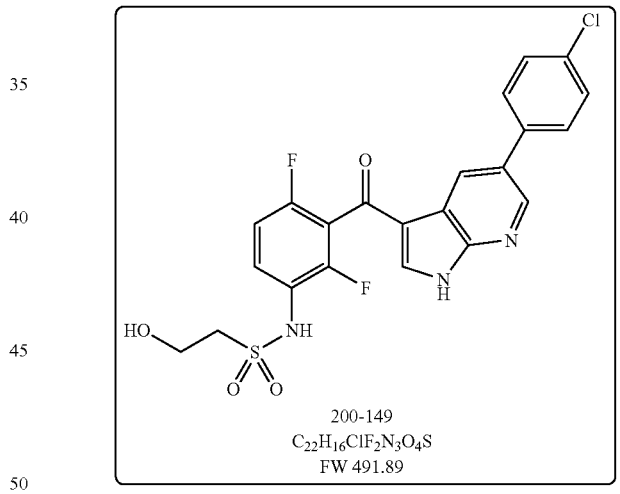

200-149
C$_{22}$H$_{16}$ClF$_2$N$_3$O$_4$S
FW 491.89

Synthesis of 200-149: Compound 200-149 is synthesized using the method shown in Scheme 8 starting from N-[3-[5-(4-chlorophenyl)-I-(2,6-dichlorobenzoyl)pyrrolo[2,3-b]pyridine-3-carbonyl]-2,4-difluorophenyl]-2-methoxy-ethanesulfonamide (200-137) and reacting it with BBr$_3$ in DCM to produce N-[3-[5-(4-chlorophenyl)-I-(2,6-dichlorobenzoyl)pyrrolo[2,3-b] pyridine-3-carbonyl]-2,4-difluorophenyl]-2-hydroxyethanesulfonamide (200-147). The protecting dichlorobenzoyl group is removed using standard conditions to produce 200-149.

EXAMPLES

Examples related to the present invention are described below. In most cases, alternative techniques can be used. The examples are intended to be illustrative and are not limiting or restrictive to the scope of the invention. In most cases, alternative techniques can be used. In some examples, the mass spectrometry results indicated for a compound may have more than one value due to the isotope distribution of an atom in the molecule, such as a compound having a bromo or chloro substituent.

Example 1

Synthesis of N-[3-[5-(4-chlorophenyl)-1H-pyrrolo[2,3-b]pyridine-3-carbonyl]-2,4-difluorophenyl]-3-hydroxypropane-1-sulfonamide (200-17)

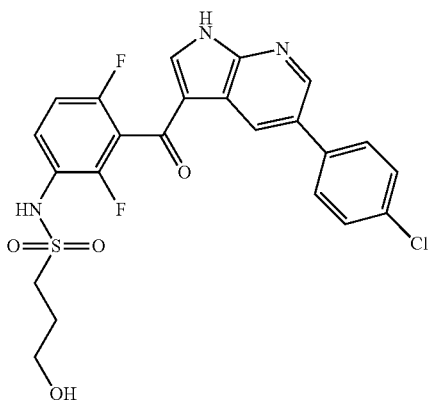 [SMILES: O=C(c1c(F)ccc(NS(=O)(=O)CCCO)c1F)c1c[nH]c2ncc(-c3ccc(Cl)cc3)cc12]

Compound 200-17 was synthesized by the procedure shown in Scheme 1.

Preparation of 2,6-difluoro-3-nitrobenzoyl chloride (2): To a 259 mL flask were added 2,6-difluoro-3-nitrobenzoic acid (8 g, 39.39 mmol), dichloromethane (80 mL), and DMF (0.3 mL). With stirring, oxalyl chloride (10.4 mL, 118.81 mmol, 3 eq) was added dropwise at room temperature under nitrogen. After addition, the mixture was stirred at room temperature under nitrogen overnight. The mixture was then concentrated under reduced pressure to get a solid residue, which was dried under vacuum and used directly in next step.

Preparation of (5-bromo-IH-pyrrolo[2,3-b]pyridin-3-yl)-(2,6-difluoro-3-nitrophenyl)methanone (3): To a 500 mL, three-necked flask were added 5-bromo-7-azaindole (7.76 g, 39.38 mmol) and 1,2-dichloroethane (DCE, 120 mL). The mixture was cooled to 0-5° C., and aluminum chloride (21 g, 157.49 mmol) was added in portions with stirring at 0-5° C. To the mixture was added a mixture of 2,6-difluoro-3nitrobenzoyl chloride (2, about 39.39 mmol) and DCE (50 mL) dropwise. During the addition, the reaction temperature was maintained below 25° C. After the addition, the reaction mixture as stirred at room temperature for 30 min and at 50° C. under nitrogen overnight. TLC analysis (EtOAc-hexanes; 1:1) showed the reaction was complete. The mixture was cooled to room temperature and poured to cold water (600 mL), followed by extraction with EtOAc (200 mL). The organic layers were washed with brine, dried ($Na_2SO_4$) and concentrated to give compound 3 as a yellow-brown solid, which was directly used in next reduction. LC-MS data: 381.60 (M+H).

Preparation of (3-amino-2,6-difluoro-phenyl)-(5-bromo-1H-pyrrolo[2,3-b]pyridin-3-yl)methanone (4): To a 1 L flask were added compound 3 (about 39.39 mmol), tetrahydrofuran (THF, 150 mL), and tin(II) chloride (22.4 g, 118.13 mmol, 3 eq). The mixture was heated to 60-65° C. under nitrogen overnight. TLC analysis (EtOAc-hexanes; 1.1) showed the reaction was complete. After the mixture was cooled to room temperature, EtOAc (200 mL) was added, followed by slow addition of 10% $NaHCO_3$ solution with much gas being released. The resulting mixture was filtered through a layer of silica gel and the solid residue was washed with EtOAc. The organic of the filtrate was washed with brine, dried ($Na_2SO_4$) and concentrated. The crude product was purified by silica gel chromatography (EtOAc-hexanes; 1:3 to 1:1) to give compound 4 as a red-brown solid (10.2 g, 74% yield over 3 steps). LC-MS data: 351.50 (M+H).

Preparation of (3-amino-2,6-difluoro-phenyl)-[5-bromo-1-(2,6-dichlorobenzoyl)pyrrolo [2,3-b] pyridin-3-yl] methadones (5): To a 250 mL flask were added compound 4 (2.2 g, 6.25 mmol), THF (70 mL), triethylamine (1.2 mL, 8.61 mmol, 1.3 eq), and 4-dimethylaminopyridine (DMAP) (40 mg). The mixture was cooled to 0-5° C., then 2,6-dichlorobenzoyl chloride (0.9 mL, 6.28 mmol) dropwise. After addition, the mixture was stirred at 0-5° C. for 1 hrs when TLC analysis (EtOAc-hexanes, 1:2) showed no presence of the starting material. The reaction was quenched with methanol (1 mL) at 0-5° C. EtOAc (100 mL) and water (100 mL) were added. The organic layer was separated, and the aqueous lay was extracted with EtOAc (100 mL). The combined organic layers were washed with brine, dried ($Na_2SO_4$), and concentrated. The residue was subjected to column chromatography (EtOAc-hexanes; 1:10 to 1:5) to give compound 5 as a yellow solid, 1.6 g, 49% yield), LC-MS data: 523.70 (M+H).

Preparation of (3-amino-2,6-difluorophenyl)-[5-(4-chlorophenyl)-1-(2,6-dichlorobenzoyl)pyrrolo [2,3-b] pyridin-3-yl]methanone (6); Compound 5 (900 mg, 1.71 mmol), 4-chlorobenzeneboronic acid (374 mg, 2.39 mmol, 1.4 eq), potassium carbonate (475 mg, 3.44 mmol, 2 eq), dioxane (10 mL), and water (6 mL) were added to a 100 mL flask. The mixture was purged with nitrogen. $PdCl_2$ (dppf) (40 mg; 0.0546 mmol. 3% eq) was added and the reaction mixture was heated to 80-82° C. and stirred for 2 hrs. TLC and HPLC showed the reaction was complete. The reaction mixture was cooled and filtered over Celite and washed with EtOAc. The organic layer of the filtrate was separated, washed with brine and water, dried ($Na_2SO_4$), and concentrated. The residue was subjected to column chromatography (EtOAc-hexanes; 1:10 to 1:4) to give compound 6 as a yellow solid, 710 mg, 75% yield). LC-MS data: 555.90 (M+H).

Preparation of sodium 3-(acetyloxy)-1-propanesulfonate (11): In a 100 mL flask were added sodium 3-hydroxy-1-propanesulfonate (5 g, 80% purity, 24.67 mmol) and acetic anhydride (12 mL, 126.95 mmol, 5.1 eq). The mixture was heated at reflux under nitrogen for 7 hrs and then cooled to room temperature. It was almost a solid. TBME (60 mL) was added, and the resultant mixture was stirred for 10 min, followed by filtration, washing with TBME and hexanes, and drying under vacuum to give compound 11 as a white solid (7.8 g).

Preparation of 3-(acetyloxy)-1-propanesulfonyl chloride (12): In a 100 mL flask was added sodium 3-(acetyloxy)-1-propanesulfonate (11, 4 g, ca 19.59 mmol), followed by dropwise addition of thionyl chloride (8 mL, 109.67 mmol, 5.6 eq). The mixture was then stirred at 68° C. under nitrogen for 5 hrs. The mixture was cooled and concentrated under reduced pressure to remove excess thionyl chloride. TBME (methyl tert-butyl ether) was added, followed by filtration and washing with TBME. The filtrate and washing were concentrated, and the resultant liquid was dried under vacuum to afford compound 12 as a pale brown liquid (1.8 g), which was used in next step without purification.

Preparation of N-[3-[5-(4-chlorophenyl)-1-(2,6-dichlorobenzoyl)pyrrolo[2,3-b]pyridine-3-carbonyl]-2,4-difluorophenyl] 3-(acetyloxy)propane-1-sulfonamide (7): To a 100 mL flask were added compound 6 (700 mg, 1.26 mmol), dioxane (15 mL), pyridine (1 mL, 12.4 mmol, 10 eq), and DMAP (20 mg), 3-(Acetyloxy)-1-propanesulfonyl chloride (12, 866 mg, 4.32 mmol, 3.4 eq) was added dropwise with stirring at room temperature. The reaction mixture is heated at 99-100° C. under nitrogen for 4 hrs when TLC analysis (EtOAc-hexanes; 1:2) and HPLC showed the reaction was complete. The mixture was cooled, and EtOAc (100 mL) was added, followed by addition of water. The organic layer was separated, and the aqueous layer was extracted with EtOAc (2 times). The combined organic layers were washed with brine, dried ($Na_2SO_4$), and concentrated to give a liquid residue. The residue was subjected to column chromatography (EtOAc-hexanes; 1:5 to 1:3) to give compound 7 as a solid (420 mg, 46% yield). LC-MS data: 720.20 (M+H).

Preparation of N-[3-[5-(4-chlorophenyl)-1H-pyrrolo[2,3-b]pyridine-3-carbonyl]-2,4-difluorophenyl]-3-hydroxypropane-1-sulfonamide (200-17): in a 100 mL flask were added compound 7 (420 mg) and methanol (5 mL). Ammonia solution (27%, 5 mL) was added dropwise with stirring. After addition, the mixture was stirred for 14 hrs at 33-35° C. TLC analysis (EtOAc-hexanes; 1:1) showed the reaction was complete. The mixture was concentrated. EtOAc (20 mL) and water (20 mL) were added. The organic layer was separated, and the aqueous lay was extracted with EtOAc (20 mL). The combined organic layers were washed with brine, dried ($Na_2SO_4$), and concentrated. The residue was subjected to column chromatography (DCM-MeOH; 95:5) to give compound 200-17 as a pale yellow solid (150 mg, 51% yield), LC-MS data: 506.10 (M+H); $^1$H NMR (DMSO-$d_6$) (ppm) 13.05 (s, broad, 1H), 9.78 (s, 1H), 8.71 (d, 1H), 8.64 (s, 1H), 8.22 (s, 1H), 7.81 (d, 2H), 7.62-7.56 (m, 3H), 7.26 (t, 1H), 4.64 (, 1H), 3.20 (m, 2H), 2.49 (m, 2H), 1.82 (m, 2H).

Example 2

Preparation of N-[3-[5-(4-chlorophenyl)-IH-1-pyrrolo [2,3-b]pyridine-3-carbonyl]-2,4-difluorophenyl]-2,3-dihydroxypropane-I-sulfonamide (200-73)

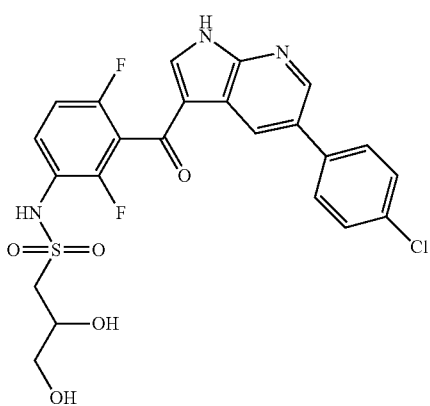 [SMILES: O=C(c1c(F)ccc(NS(=O)(=O)CC(O)CO)c1F)c1c[nH]c2ncc(-c3ccc(Cl)cc3)cc12]

Compound 200-73 was synthesized starting from (3-amino-2,6-difluorophenyl)-[5-(4-chlorophenyl)-1-(2,6-dichlorobenzoyl)pyrrolo [2,3-b] pyridin-3-yl] methanone (6) by the synthetic procedure shown in Scheme 2.

Preparation of prop-2-ene-1-sulfonyl chloride (22): In a 200 flask was added sodium prop-2-ene-1-sulfonate (21, 4 g 27.75 mmol), followed by dropwise addition of thionyl chloride (10 mL, 137.09 mmol, 4.9 eq) at room temperature. The mixture was then stirred at 65° C. under nitrogen for 1 hrs. Due to stirring difficulty, benzene (5 mL) and thionyl chloride (2 mL) were added. The mixture was stirred at 65° C. under nitrogen, overnight. After the mixture was cooled to room temperature, TBME (30 mL) and sodium sulfate were added. The mixture was stirred for 30 min and filtered through a layer of silica gel. The filtrate was concentrated to give compound 22 as a pale brown liquid (2.95 g, 76 yield), which was used in next step without purification.

Preparation of N-[3-[5-(4-chlorophenyl)-I-(2,6-dichlorobenzoyl)pyrrolo[2,3-b] pyridine-3-carbonyl]-2,4-difluoro-phenyl] prop-2-ene-1-sulfonamide (23): To a 100 mL flask were added compound 6 (370 mg, 0.664 mmol), dioxane (15 mL), pyridine (0.5 mL, 6.18 mmol, 9.3 eq), and DMAP (20 mg). Prop-2-ene-1-sulfonyl chloride (22, 400 mg, 2.85 mmol, 4.3 eq) was added dropwise with stirring at room temperature. The reaction mixture is heated at 85° C. under nitrogen for 2 hrs when TLC analysis (EtOAc-hexanes, 1:2) and HPLC showed the reaction was complete. The mixture was cooled, and EtOAc (100 mL) was added, followed by addition of water. The organic layer was separated, and the aqueous layer was extracted with EtOAc (2 times). The combined organic layers were washed with brine, dried ($Na_2SO_4$), and concentrated to give a liquid residue. The residue was subjected to column chromatography (EtOAc-hexanes; 1:5 to 1:3) to give compound 23 as a yellow-brown solid (410 mg, 93% yield). LC-MS data: 659.90, 663.10 (M+H).

Preparation of N-[3-[5-(4-chlorophenyl)-I-(2,6-dichlorobenzoyl)pyrrolo[2,3-b] pyridine-3-carbonyl]-2,4-difluoro-phenyl] 2,3-dihydroxypropane-1-sulfonamide (24): To a 100 mL flask were added compound 23 (500 mg, 0.757 mmol), acetone (24 mL), N-methylmorpholine N-oxide (178 mg, 1.52 mmol, 2 eq), and water (6 mL) at room temperature. Osmium tetroxide solution (4%, 4 mL) was added dropwise with stirring. The reaction mixture is stirred at room temperature overnight when TLC analysis (EtOAc-hexanes; 1:2) showed the reaction was complete. EtOAc (100 mL) was added, followed by addition of water. The organic layer was separated, and the aqueous layer was extracted with EtOAc (2 times). The combined organic layers were washed with brine, dried ($Na_2SO_4$), and concentrated to give a liquid residue. The residue was subjected to column chromatography (EtOAc-hexanes; 2:1) to give compound 24 as a pale brown solid (300 mg, 57% yield). LC-MS data: 694.00, 696.10 (M+H).

Preparation of N-[3-[5-(4-chlorophenyl)-IH-pyrrolo[2,3-b]pyridine-3-carbonyl]-2,4-difluorophenyl]-2,3-dihydroxypropane-I-sulfonamide (200-73): In a 100 mL flask were added compound 24 (300 mg) and THF (2 mL), and methanol (5 mL). Ammonia solution (27%, 5 mL) was added dropwise with stirring. After addition, the mixture was stirred for 3 hrs at 33-35° C. TLC analysis (EtOAc only) showed the reaction was complete. The mixture was concentrated. EtOAc (20 mL) and water (20 mL) were added. The organic layer was separated, and the aqueous lay was extracted with EtOAc (20 mL). The combined organic layers were washed with brine, dried ($Na_2SO_4$), and concentrated. The residue was subjected to column chromatography (DCM-MeOH; 95:5) to give compound 200-73 as an off-white solid (120 mg, 53% yield). LC-MS data: 521.80, 523.90 (M+H); $^1$H NMR (DMSO-$d_6$) (ppm) 13.00 (s, broad, 1H), 9.64 (s, 1H), 8.71 (d, 1H), 8.65 (s, 1H), 8.19 (s, 1H), 7.81 (d, 2H), 7.62-7.56 (m, 3H), 7.26 (t, 1H), 5.08 (d, 1H), 4.81 (t, 1H), 4.01 (m, 2H), 3.30 (m, 2H), 3.05 (m, 1H).

Example 3

Preparation of N-[3-[5-(4-chlorophenyl)-IH-1-pyrrolo[2,3-b]pyridine-3-carbonyl]-2,4-difluorophenyl] prop-1-ene-I-sulfonamide (200-93)

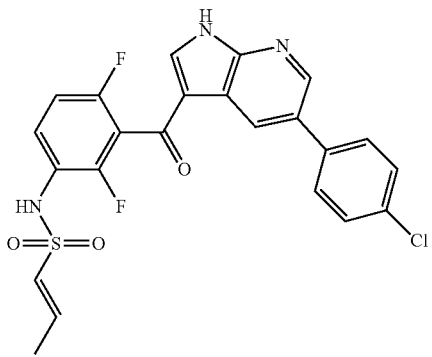 [SMILES: C/C=C/S(=O)(=O)Nc1ccc(F)c(C(=O)c2c[nH]c3ncc(-c4ccc(Cl)cc4)cc23)c1F]

Compound 200-93 a synthesized by the procedure shown in Scheme 3.

Preparation of 1-mercapto-2-(benzyloxy)propane (34): In a 250 mL flask were added propene oxide (2 g, 34.43 mmol) and thiobenzoic acid (4.76 g, 34.44 mmol), by dropwise addition of triethylamine (0.4 mL, 2.86 mmol) at room temperature. It was observed that reaction occurred suddenly when 0.2 mL of triethylamine was added. After stirring at room temperature for 15 min, TLC showed reaction was complete. Silica gel (18 g) was added. The mixture was then stirred at 65° C. under nitrogen overnight. TLC showed 2-hydroxythioester (33) was mainly converted to 1-mercapto-2-benzyloxypropane. After the mixture was cooled to room temperature, TBME (50 mL) was added. The mixture was stirred for 30 min and filtered through a layer of silica gel. The filtrate was concentrated to give compound 34 as a pale brown liquid (5.8 g), which was used in next step without purification.

Preparation of 2-(benzyloxy)-1-propanesulfonyl chloride (35): NCS (5.44 g, 40.74 mmol, 4 eq) was added to a mixture of 2N HCl solution and MeCN (8 mL/18 mL). The mixture was cooled to 10° C. A solution of 34 (2 g, 10.19 mmol) was added dropwise below 20° C. After addition, the mixture was stirred below 20° C. for 20 min. TBME (30 mL) was added. The organic layer was separated and washed with 12% NaOH solution (3×8 mL), dried ($Na_2SO_4$), concentrated, and purified by column purification (EtOAc-hexanes; 1:6) to give compound 35 as a pale yellow liquid (3.8 g).

Preparation of N-[3-[5-(4-chlorophenyl)-I-(2,6-dichlorobenzoyl)pyrrolo[2,3-b] pyridine-3-carbonyl]-2,4-difluoro-phenyl] prop-1-ene-1-sulfonamide (36): To a 100 mL flask were added compound 6 (370 mg, 0.664 mmol), dioxane (15 mL), pyridine (0.5 mL, 6.18 mmol, 9.3 eq), and DMAP (20 mg). 2-(Benzyloxy)-1-propanesulfonyl chloride (35, 700 mg, 2.66 mmol, 4 eq) was added dropwise with stirring at room temperature. The reaction mixture is heated at 85° C. under nitrogen for 8 hrs when TLC analysis (EtOAc-hexanes; 1:2) and HPLC showed the reaction was complete. The mixture was cooled, and EtOAc (100 mL) was added, followed by addition of water. The organic layer was separated, and the aqueous layer was extracted with EtOAc (2 times). The combined organic layers were washed with brine, dried ($Na_2SO_4$), and concentrated to give a liquid residue. The residue was subjected to column chromatography (EtOAc-hexanes; 1:5 to 1:3) to give compound 36 as a pale brown solid (350 mg, 80% yield). LC-MS data: 659.90, 663.10 (M+H).

Preparation of N-[3-[5-(4-chlorophenyl)-IH-1-pyrrolo[2,3-b]pyridine-3-carbonyl]-2,4-difluorophenyl] prop-1-ene-I-sulfonamide (200-93): In a 100 mL flask were added compound 24 (300 mg) and THF (2 mL), and methanol (5 mL). Ammonia solution (27%, 5 mL) was added dropwise with stirring. After addition, the mixture was stirred for 3 hrs at 33-35° C. TLC analysis (EtOAc only) showed the reaction was complete. The mixture was concentrated. EtOAc (20 mL) and water (20 mL) were added. The organic layer was separated, and the aqueous lay was extracted with EtOAc (20 mL). The combined organic layers were washed with brine, dried ($Na_2SO_4$), and concentrated. The residue was subjected to column chromatography (DCM-MeOH; 95:5) to give a mixture of two isomers (cis- and trans-) of compound 200-93 as a pale yellow brown solid (35 mg). LC-MS data: 488.0, 490.20 (M+H). 200-93 isomers were further separated by HPLC on a YMC-Pack ODS column (100×20 mm, 50 μm, 120 A) eluted with methanol (B) and water (A) in a stepwise gradient over 20 min running time. The two isomers were named as 200-93a and 200-93b with HPLC retention time of 11 and 9 min, respectively.

Example 4

Preparation of N-[3-[5-(4-chlorophenyl)-1-(2,6-dichlorobenzoyl)pyrrolo[2,3-b] pyridine-3-carbonyl]-2,4-difluoro-phenyl]-2-hydroxypropane-1-sulfonamide (00-115)

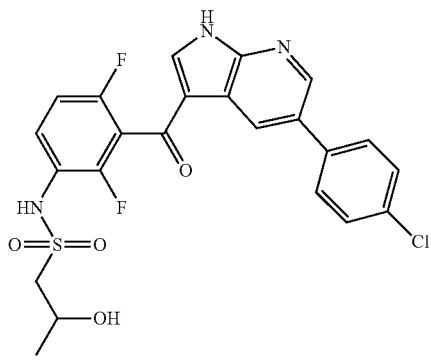 [SMILES: CC(O)CS(=O)(=O)Nc1ccc(F)c(C(=O)c2c[nH]c3ncc(-c4ccc(Cl)cc4)cc23)c1F]

Compound 200-115 was synthesized starting from (3-amino-2,6-difluorophenyl)-[5-(4-chlorophenyl)-1-(2,6-dichlorobenzoyl)pyrrolo [2,3-b] pyridin-3-yl]methanone (6) by the synthetic procedure shown in Scheme 4.

Preparation of sodium 2-oxopropanesulfonate (200-105): Chloroacetone (8 mL, 0.10 mol), $Na_2SO_3$ (14.5 g, 0.115 mol) and $H_2O$ (100 mL) were mixed in a flask equipped with a condenser. The mixture was refluxed with stirring for 20 hrs, after which the mixture was evaporated to dryness. Ethanol (30 mL) was added to the residue, followed by concentration. TBME-hexanes (1:1; 30 mL) were added. After stirring a while, filtration, washing with hexanes, and drying under reduced pressure gave a white solid (28 g), which contained the product sodium 2-oxopropanesulfonate and sodium chloride with about 70% purity.

Preparation of 2-Oxopropanesulfonyl chloride (200-110): To a mixture of toluene (5 mL) and $POCl_3$ (5 mL) at 5° C. was added sodium 2-oxopropanesulfonate (4 g, about 70% purity) in portions. The mixture was then heated (oil bath 110° C.) for 3 hrs. The solvent was removed by evaporation, the product was dissolved in DCM (15 mL), and the mixture was filtered. The filtrate was concentrated to yield the title compound as a dark brown liquid (1.5 g), which was used without further purification.

Preparation of N-[3-[5-(4-chlorophenyl)-I-(2,6-dichlorobenzoyl)pyrrolo[2,3-b] pyridine-3-carbonyl]-2,4-difluoro-phenyl]-2-oxopropane-1-sulfonamide (200-111): To a 100 mL flask were added compound 6 (450 mg, 0.81 mmol), dioxane (15 mL), pyridine (0.6 mL, 7.42 mmol, 9.2 eq), and DMAP (30 mg). 2-Oxopropanesulfonyl chloride (510 mg, 3.26 mmol, 4 eq) was added dropwise with stirring at room temperature. The reaction mixture was heated at 85° C. under nitrogen for 2 hrs when TLC analysis (EtOAc-hexanes; 1:2) and HPLC showed the reaction was complete. The mixture was cooled, and EtOAc (100 mL) was added, followed by addition of water. The organic layer was separated, and the aqueous layer was extracted with EtOAc (2 times). The combined organic layers were washed with brine, dried ($Na_2SO_4$), and concentrated to give a liquid residue. The residue was subjected to column chromatography (EtOAc-hexanes: 1:5 to 1:3) to give compound 200-111 as a pale brown solid (490 mg, 89% yield). LC-MS data; 676 (M+H).

Preparation of N-[3-[5-(4-chlorophenyl)-I-(2,6-dichlorobenzoyl)pyrrolo[2,3-b] pyridine-3-carbonyl]-2,4-difluoro-phenyl]-2-hydroxypropane-1-sulfonamide (200-113): To a mixture of compound 200.111 (219 mg, 0.81 mmol) and methanol (30 mL) and THF (5 mL) at 0° C. was added a solution of NaBH4 (13 mg) in MeOH (5 mL) dropwise. After addition, the mixture was stirred at 0-5° C. for 10 min and TLC analysis (EtOAc-hexanes: 1:2) showed the absence of the starting material. Water (2 mL) was, added to quench the reaction. EtOAc (100 mL) was added, followed by addition of water. The organic layer as separated, and the aqueous layer was extracted with EtOAc (2 times). The combined organic layers were washed with brine, dried ($Na_2SO_4$), and concentrated, to give a liquid residue. The residue was subjected to column chromatography (EtOAc-hexanes; 1:4 to 1:2) to give 200-113 as an off-white solid (110 mg, 51%). LC-MS data: 678.2 (M+H).

Preparation of N-[3-[5-(4-chlorophenyl)-I-(2,6-dichlorobenzoyl)pyrrolo[2,3-b] pyridine-3-carbonyl]-2,4-difluoro-phenyl]-2-hydroxypropane-1-sulfonamide (200-115): In a 100 mL flask were added compound 200-113 (95 mg), methanol (5 mL), and THF (3 mL). Ammonia solution (27%, 4 mL) was added dropwise with stirring. After addition, the mixture was stirred for 3 hrs at 33-35° C. TLC analysis (EtOAc-hexanes; 1:1) showed the reaction was complete, EtOAc and sodium sulfate ($Na_2SO_4$) were added. After stirring a while, the mixture was filtered, and the filtrate was concentrated. The residue was subjected to column chromatography (EtOAc-hexanes; 1:3, then EtOAc only) to give 200-115 as a pale brown solid (48 mg) LC-MS data: 506.30 (M+H); H NMR (DMSO-$d_6$) (ppm) 13.02 (s, broad, 1H), 9.75 (s, 1H), 8.71 (d, 1H), 8.64 (s, 1H), 8.22 (s, 1H), 7.81 (d, 2H), 7.62-7.56 (m, 3H), 7.26 (t, 1H), 5.10 (s, 1H), 4.10 (m, 1H), 3.12 (m, 2H), 1.22 (d, 3H).

Example 5

Preparation of N-[3-[5-(4-chlorophenyl)-I-(2,6-dichlorobenzoyl)pyrrolo[2,3-b] pyridine-3-carbonyl]-2,4-difluoro-phenyl]-2-oxopropane-1-sulfonamide (200-117)

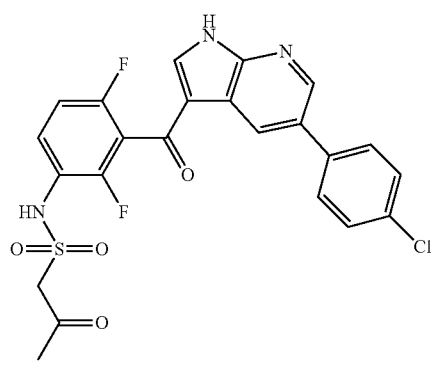 [SMILES: CC(=O)CS(=O)(=O)Nc1ccc(F)c(C(=O)c2c[nH]c3ncc(-c4ccc(Cl)cc4)cc23)c1F]

Compound 200-117 was synthesized starting from N-[3-[5-(4-chlorophenyl)-I-(2,6-dichlorobenzoyl)pyrrolo[2,3-b] pyridine-3-carbonyl]-2,4-difluoro-phenyl]-2-oxopropane-1-sulfonamide (200-111) by the synthetic procedure shown in Scheme 5.

Preparation of N-[3-[5-(4-chlorophenyl)-I-(2,6-dichlorobenzoyl)pyrrolo[2,3-b] pyridine-3-carbonyl]-2,4-difluoro-phenyl]-2-hydroxypropane-1-sulfonamide (200-117): To a 100 mL flask were added compound 200-111 (110 mg), methanol (5 mL), and THF (3 mL). Ammonia solution (27%, 4 mL) was added dropmise with stirring. After addition, the mixture was stirred for 3 hrs at 33-35° C. TLC analysis (EtOAc-hexanes, 1:1) showed the reaction was complete. EtOAc and sodium sulfate ($Na_2SO_4$) were added. After stirring a while, the mixture was filtered, and the filtrate was concentrated. The residue was subjected to column chromatography (EtOAc-hexanes; 1:3, then 2:1) to give 200-117 as an off-white solid (49 mg). LC-MS data: 503.90 (M+H); $^1$H NMR (DMSO-$d_6$) (ppm) 13.02 (s, broad, 1H), 10.05 (s, 1H), 8.71 (d, 1H), 8.64 (s, 1H), 822 (s, 1H), 7.81 (d, 2H), 7.62-7.56 (m, 3H), 7.26 (t, 1H), 4.40 (s, 2H), 2.22 (s, 3H).

Example 6

Preparation of N-[3-[5-(4-chlorophenyl)pyrrolo[2,3-b] pyridine-3-carbonyl]-2,4-difluoro-phenyl]-3-methoxypropane-1-sulfonamide (200-123)

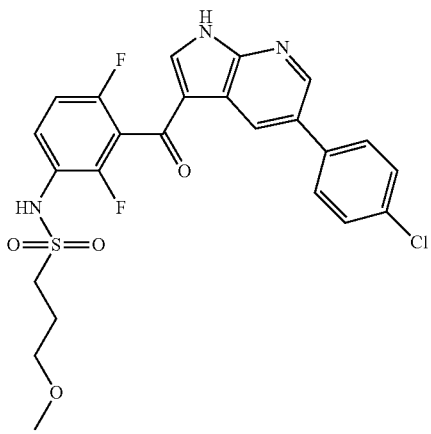 [SMILES: COCCCS(=O)(=O)Nc1ccc(F)c(C(=O)c2c[nH]c3ncc(-c4ccc(Cl)cc4)cc23)c1F]

Compound 200-123 was synthesized starting from 3-amino-2,6-difluorophenyl)-[5-(4-chlorophenyl)-1-(2,6-dichlorobenzoyl)pyrrolo [2,3-b] pyridin-3-yl]methanone (6) by the synthetic procedure shown in Scheme 6.

Preparation of sodium 3-methoxypropane-1-sulfonate (200-119): 1-Bromo-3-methoxypropane (7.5 g, 49.01 mmol), $Na_2SO_3$ (6.2 g, 49.19 mmol) and $H_2O$ (50 mL) were mixed in a flask equipped with a condenser. The mixture was refluxed with stirring for 20 hrs, after which the mixture was evaporated to dryness. Ethanol (30 mL) was added to the residue followed by concentration. TBME-hexanes (1:1, 30 mL) were added. Following stirring, filtration, washing with hexanes, and drying under vacuum gave a white solid (10.5 g), which contained the product sodium 3-methoxypropane-1-sulfonate and sodium bromide with about 63% purity.

Preparation of 3-Methoxypropane-1-sulfonyl chloride (200-120): To a mixture of toluene (16 mL) and thionyl chloride (10 mL) at 5° C. was added sodium 3-methoxypropane-1-sulfonate (200-119) (5 g, about 63% purity) in portions. The mixture was heated to 80° C. for 4 hrs. The mixture was cooled and concentrated, and the residue was dissolved in DCM (15 mL). The mixture as filtered and the filtrate concentrated to yield the 200-120 as a brown liquid (1.95 g), which was used without further purification.

Preparation of N-[3-[5-(4-chlorophenyl)-1-(2,6-dichlorobenzoyl)pyrrolo[2,3-b] pyridine-3-carbonyl]-2,4-difluoro-phenyl]-3-methoxypropane-1-sulfonamide (200-121): To a 100 mL flask were added compound 6 (250 mg, 0.45 mmol), dioxane (15 mL), pyridine (0.6 mL, 7.42 mmol, 16.4 eq), and DMAP (25 mg). 3-methoxypropane-1-sulfonyl chloride (200-120) (200 mg, 1.16 mmol, 2.6 eq) was added dropwise with stirring at room temperature. The reaction mixture was heated at 85° C. under nitrogen for 6 hrs whereby TLC (EtOAc-hexanes, 1:2) and HPLC showed the reaction to be complete. The mixture was cooled and EtOAc (100 mL) added followed by addition of water. The organic layer was separated and the aqueous layer extracted with EtOAc (2 times). The combined organic layers were washed with brine, dried with $Na_2SO_4$, and concentrated to give a liquid residue. The residue was subjected to column chromatography (EtOAc-hexanes, 1:6 to 1:3) to give compound 200-121 as a pale brown solid (150 mg, 48% yield). LC-MS data. 682.00 (M+H).

Preparation of N-[3-[5-(4-chlorophenyl)pyrrolo[2,3-b] pyridine-3-carbonyl]-2,4-difluorophenyl]-3-methoxypropane-1-sulfonamide (200-123): In a 100 mL flask were added compound 200-121 (150 mg, 0.22 mmol), methanol (4 mL), and THF (2 mL). Ammonia solution (27%, 4 mL) was added dropwise with stirring. After addition, the mixture was stirred for 3 hrs at 33-35° C. TLC analysis (EtOAc-hexanes, 1:1) showed the reaction to be complete. EtOAc and sodium sulfate ($Na_2SO_4$) were added to the mixture. After stirring a period of time, the mixture was filtered and the filtrate concentrated. The residue was subjected to column chromatography (EtOAc-hexanes, 1:2, then 2:1) to give compound 200-123 as an off-white solid (48 mg). LC-MS data: 520.00 (M+H): $^1$H NMR (DMSO-$d_6$) (ppm) 13.02 (s, broad, 1H), 9.85 (s, 1H), 8.71 (s, 1H), 8.64 (d, 1H), 8.22 (s, 1H), 7.81 (d, 2H), 7.62-7.56 (m, 3H), 7.26 (t, 1H), 3.40 (t, 2H), 3.56 (s, 3H), 1.95 (m, 2H). 1.20 (t, 2H).

Example 7

Preparation of N-[3-[5-(4-chlorophenyl)pyrrolo[2,3-b] pyridine-3-carbonyl]-2,4-difluorophenyl]-2-methoxyethanesulfonamide (200-139)

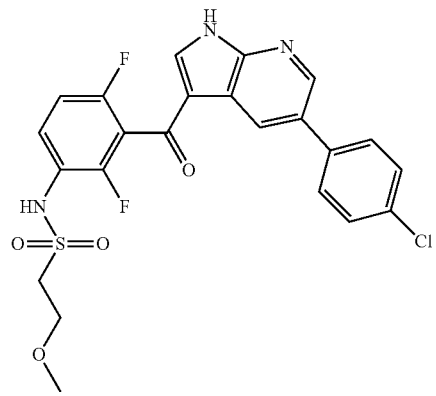 [SMILES: COCCS(=O)(=O)Nc1ccc(F)c(C(=O)c2c[nH]c3ncc(-c4ccc(Cl)cc4)cc23)c1F]

Compound 200-139 was synthesized starting from 3-amino-2,6-difluorophenyl)-[5-(4-chlorophenyl)-1-(2,6-dichlorobenzoyl)pyrrolo [2,3-b] pyridin-3-yl]methanone (6) by the synthetic procedure shown in Scheme 7.

Preparation of sodium 2-methoxyethanesulfonate (200-135): 1-Bromo-2-methoxyethane (7.5 g, 53.96 mmol), $Na_2SO_3$ (6.8 g, 53.95 mmol) and $H_2O$ (50 mL) were mixed in a flask equipped with a condenser. The mixture was refluxed with stirring for 20 hrs. The mixture was evaporated to dryness. Ethanol (30 mL) was added to the residue, followed by concentration. TBME-hexanes (1:1, 40 mL) were added. After stirring for a period of time, filtration, washing with hexanes, and drying under vacuum gave white solid (14 g) comprising the product sodium 2-methoxyethanesulfonate (200-135) (61% purity) and sodium bromide.

Preparation of 2-Methoxyethanesulfonyl chloride (200-136): To a mixture of thionyl chloride (15 mL) at 5° C. was added sodium 2-methoxyethanesulfonate (200-135) (5 g, about 61% purity) in portions, followed by addition of 3 drops of DMF. The mixture was stirred at room temperature for 20 min followed by heating at 80° C. under nitrogen for 6 hrs. The mixture was cooled and concentrated, and the residue was dissolved in TBME (15 mL). The mixture was filtered and the filtrate concentrated to yield the title compound 200-136 as a pale brown liquid (1.85 g), which was used without further purification.

Preparation of N-[3-[5-(4-chlorophenyl)-I-(2,6-dichlorobenzoyl)pyrrolo[2,3-b] pyridine-3-carbonyl]-2,4-difluorophenyl]-2-methoxyethanesulfonamide (200-137): To a 100 mL flask were added compound 6 (95 mg, 0.17 mmol), dioxane (15 mL), pyridine (0.5 mL), and DMAP (25 mg). 2-methoxyethanesulfonyl chloride (200-136) (100 mg, 0.63 mmol, 3.7 eq) was added dropwise with stirring at room temperature. The resultant reaction mixture was heated at 85° C. under nitrogen for 6 hrs where TLC (EtOAc-hexanes, 1:2) and HPLC showed the reaction to be complete. The mixture was cooled and EtOAc (100 mL) added followed by addition of water. The organic layer was separated, and the aqueous layer extracted with EtOAc (twice). The combined organic layers were washed with brine, dried with $Na_2SO_4$, and concentrated to give a liquid residue. The residue was purified by column chromatography (EtOAc-hexanes, 1:6 to 1:3) to give compound 200-137 as a pale brown solid (59 mg, 51% yield). LC-MS data: 678.00 (M+H).

Preparation of N-[3-[5-(4-chlorophenyl)pyrrolo[2,3-b] pyridine-3-carbonyl]-2,4-difluorophenyl]-2-methoxyethanesulfonamide (200-139): In a 100 mL flask were added compound 200-137 (50 mg, 0.074 mmol), methanol (5 mL), and THF (1 mL). Ammonia solution (27%, 2 mL) was added dropwise with stirring. After addition, the mixture was stirred for 3 hrs at 33-35° C. and left to stir overnight at room temperature. TLC analysis (EtOAc-hexanes, 1:1) showed the reaction was complete. EtOAc and sodium sulfate ($Na_2SO_4$) were added. After stirring for a period of time, the mixture was filtered and the filtrate concentrated. The residue was purified by column chromatography (EtOAc-hexanes, 1:2, then 3:1) to give compound 200-139 as a pale yellow-brown solid (28 mg). LC-MS data: 506.00 (M+H); $^1$H NMR (DMSO-$d_6$) (ppm) 13.02 (s, broad, 1H), 8.71 (s, 1H), 8.64 (s, 1H), 8.22 (s, 1H), 7.81 (d, 2H), 7.62-7.56 (m, 3H), 7.26 (t, 1H), 3.60 (t, 2H), 3.36 (s, 3H), 2.42 (t, 2H).

Example 8

Preparation of N-[3-[5-(4-chlorophenyl)pyrrolo[2,3-b] pyridine-3-carbonyl]-2,4-difluorophenyl]-2-hydroxyethanesulfonamide (200-149)

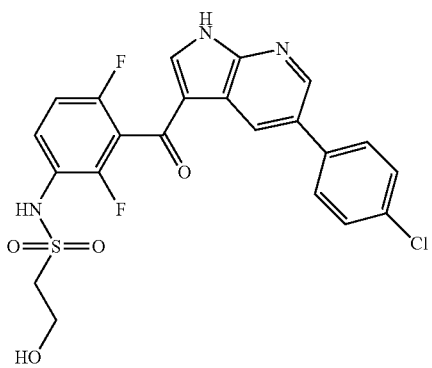 [SMILES: O=C(c1c(F)ccc(NS(=O)(=O)CCO)c1F)c1c[nH]c2ncc(-c3ccc(Cl)cc3)cc12]

Compound 200-149 was synthesized starting from N-[3-[5-(4-chlorophenyl)-I-(2,6-dichlorobenzoyl)pyrrolo[2,3-b] pyridine-3-carbonyl]-2,4-difluorophenyl]-2-methoxyethanesulfonamide (200-137) by the synthetic procedure shown in Scheme 8.

Preparation of N-[3-[5-(4-chlorophenyl)-1-(2,6-dichlorobenzoyl)pyrrolo[2,3-b] pyridine-3-carbonyl]-2,4-difluorophenyl]-2-hydroxyethanesulfonamide (200-147): A solution of compound 200-137 (250 mg, 0.368 mmol) in DCM was cooled to −64° C., $BBr_3$ (0.2 mL, 2.11 mmol) was added dropwise with stirring. Following addition, the mixture was stirred for 15 min at −64° C. and for 3 hrs at room temperature. EtOAc (50 mL) was added followed by addition of cold water. The organic layer was separated and the aqueous layer extracted with EtOAc (twice). The combined organic layers were washed with brine, dried with $Na_2SO_4$, and concentrated to give a liquid residue. The residue eras purified by column chromatography (EtOAc-hexanes, 1:3 to 1:1) to give compound 200-147 as a pale brown oil (120 mg, 49% yield). LC-MS data: 664.17 (M+H).

Preparation of N-[3-[5-(4-chlorophenyl)pyrrolo[2,3-b] pyridine-3-carbonyl]-2,4-difluorophenyl]-2-hydroxyethanesulfonamide (200-149): In a 100 mL flask were added compound 200-147 (120 mg, 0.18 mmol), methanol (5 mL), and THF (2 mL). Ammonia solution (27%, 2 mL) was added dropwise with stirring. After addition, the mixture was stirred for 2 hrs at 33-35° C. TLC analysis (EtOAc-hexanes, 1:1) showed the reaction was complete. EtOAc and sodium sulfate ($Na_2SO_4$) were added. After stirring for a period of time, the mixture was filtered and the filtrate concentrated. The residue was purified by column chromatography (EtOAc-hexanes, 1:2, then DCM-MeOH, 20:1) to give compound 200-149 as an off-white solid (58 mg) LC-MS data: 492.3 (M+H): $^1$H NMR (DMSO-$d_6$) (ppm) 13.02 (s, broad, 1H), 9.78 (s, 1H), 8.71 (s, 1H), 8.64 (s, 1H), 8.22 (s, 1H), 7.81 (d 2H), 7.62-7.56 (m, 3H), 7.26 (t, 1H), 5.01 (s, 1H), 3.80 (t, 2H), 2.50 (t, 2H).

Example 9

Protein Kinase Inhibition Studies

Off-chip Mobility Shift Assay (MSA) by Carna Biosciences, Inc (Natick, Mass.) was used for measuring the kinase activity and inhibition.
1) The 5 μL of ×4 compound solution, 5 μL of ×4 Substrate/ATP/Metal solution, and 10 μL of ×2 kinase solution were prepared with assay buffer (20 mM HEPES, 0.01% Triton X-100, 2 mM DTT, pH 7.5) and mixed, and incubated in a well of polypropylene 384 well microplate for 1 or 5 hour(s)* at room temperature. (*; depending on kinase)
2) 70 μL of Termination Buffer (QuickScout Screening Assist MSA; Carna Biosciences) was added to the well.
3) The reaction mixture was applied to LabChip system (Perkin Elmer), and the product and substrate peptide peaks were separated and quantitated.
4) The kinase reaction was evaluated by the product ratio calculated from peak heights of product (P) and substrate (S) peptides (P/(P+S)).
5) The reaction conditions were followed according to assay protocols of Carna Biosciences, Inc (BMA 3F, 1-5-5 Minatojima-Minamimachi, Chuo-ku, Kobe 650-0047, Japan; www.carnabio.com).
6) Data analysis: The readout value of reaction control (complete reaction mixture) was set as a 0% inhibition, and the readout value of background (Enzyme (−)) was set as 100% inhibition, then the percent inhibition of each test solution was calculated.

TABLE 1

Inhibition of kinase activities by compound 200-17

| Inhibitor concentration | Inhibition category | Kinases |
|---|---|---|
| 1 μM | >50% inhibition | BRK, FGR, PDGFRα(V561D), DDR2, LYNa, SRM, PDGFRα, LCK, DDR1, KDR, ACK, JAK1, LYNb, KIT, CSK, YES, KIT(V560G), BLK, MST1, JAK2, RET(S891A), SRC, FYN(isoform a), RET(G691S), FYN(isoform b), PDGFRβ, RET, FLT4, RET(Y791F), skMLCK, FRK, MST2, FLT1, AurA, FLT3, JAK3, RET(M918T), WNK3, p38β, FGFR2, MNK1, MNK2, PIK3CA/PIK3R1, PDGFRα(D842V), MET, FGFR1, BRAF(V600E), MAP2K5, KIT(D816E), ALK, FGFR3, RAF1, MAP2K3, HER4, KIT(D816V), Erk5, EGFR, YES(T348I), KIT(V654A) |
|  | <50% inhibition | KIT(D816Y), PDGFRα(T674I), BRAF, ABL, HER2, EPHA5, ROCK2, KIT(T670I), PKD3, MST4, MAP2K1, MAP2K2, MST3, ROCK1, IGF1R, PKD2, MAP2K6, Erk2, PKD1, MAP2K7, Erk1, MAP2K4, BTK |
| 0.1 μM | >50% inhibition | SRM, BRK, FGR, LCK, JAK1, CSK, PDGFRα, DDR2, PDGFRα(V561D), MST1, KIT, YES, LYNa, DDR1, LYNb, RET(S891A), BLK, KDR, SRC, JAK2, KIT(V560G) |
|  | <50% inhibition | ACK, RET, FYN(isoform a), MST2, RET(G691S), RET(Y791F), PDGFRβ, JAK3, FYN(isoform b), RET(M918T), BTK |
| 0.01 μM | >30% inhibition | SRM, BRK, FGR, LCK, KIT, JAK1 |
|  | <30% inhibition | PDGFRα, CSK, PDGFRα(V561D), YES, RET(S891A), LYNa, DDR1, LYNb, BLK, RET, SRC, DDR2, KDR, RET(G691S), RET(M918T), MST1, JAK3, ACK, MST2, PDGFRβ, RET(Y791F), KIT(V560G), FYN(isoform a), FYN(isoform b), JAK2, BTK |

TABLE 2

Inhibition of kinase activities by compounds 200-73, 200-93a, 200-93b, 200-115, 200-117, 200-123, 200-139

| Inhibitor | Inhibition category | Kinase |
|---|---|---|
| 200-73 at 0.1 μM | >30% inhibition | SRM, RAF1, JAK1, BRK |
|  | <30% inhibition | LCK, KIT FGR, BRAF, MNK2, MAPKAPK2, MNK1, PIK3CA/PIK3R1, PDGFRα, LYNa, JAK3, BRAF(V600E), FLT3, JAK2, AurA, EGFR, LYNb, BTK, MLK1, KIT(V560G), HER2, SRC, ABL, PDGFRβ, Erk5, KIT(T670I)), MAP3K4, ROS, BMX, EGFR(L858R), IGF1R, MET, HER4, AXL, AKT2, RET, RON, PIM2, FGFR3, KIT(D816V), ABL(T315I), PIM3, JNK1, MAP2K1, AKT3, ABL(E255K), AKT1, KDR, ALK, PIM1, JNK2, JNK3, Erk2, Erk1, AurB, PKACα, MAP2K2, FAK, FGFR2 |
| 200-115 at 0.1 μM | >30% inhibition | SRM, BRK, RAF1, PDGFRα, FGR, LCK |
|  | <30% inhibition | LYNa, KIT, BRAF(V600E), JAK1, LYNb, MNK2, SRC, PIK3CA/PIK3R1, KDR, EGFR, MLK1, RON, MAPKAPK2, PDGFRβ, KIT(V560G), ABL, FLT3, KIT(T670I), HER2, MNK1, MET, MAP3K4, AKT2, AurA, BMX, JAK2, ROS, PIM2, AXL, EGFR(L858R), KIT(D816V), RET, AurB, FGFR3, HER4, IGF1R, JAK3, BTK, ABL(T315I), FGFR2, Erk5, AKT1, JNK1, AKT3, MAP2K1, ALK, BRAF, ABL(E255K), JNK3, PIM3, JNK2, PKACα, Erk2, FAK, Erk1, MAP2K2, PIM1 |
| 200-117 at 0.1 μM | >30% inhibition | BRK, SRM, LCK, FGR, RAF1, LYNa, PDGFRα, LYNb, MNK2 |
|  | <30% inhibition | KIT, BRAF(V600E), JAK1, SRC, PIK3CA/PIK3R1, KDR, EGFR, MLK1, RON, MAPKAPK2, PDGFRβ, KIT(V560G), ABL, FLT3, KIT(T670I), HER2, MNK1, MET, MAP3K4, AKT2, AurA, BMX, JAK2, ROS, PIM2, AXL, EGFR(L858R), KIT(D816V), RET, AurB, FGFR3, HER4, IGF1R, JAK3, BTK, ABL(T315I), FGFR2, Erk5, AKT1, JNK1, AKT3, MAP2K1, ALK, BRAF, ABL(E255K), JNK3, PIM3, JNK2, PKACα, ErK2, FAK, Erk1, MAP2K2, PIM1 |
| 200-93a at 0.01 μM | >20% inhibition | PDGFRα, PDGFRβ |
|  | >30% inhibition | PDGFRα(V561D), KIT(V560G), BRK, JAK1, KIT, PDGFRα(T674I), LCK, SRM, SRC, PDGFRα(D842V), FGR, KIT(T670I), JAK3, BRAF(V600E), JAK2, RAF1, BRAF, KIT(D816V) |
| 200-93b at 0.01 μM | >20% inhibition | SRM, BRK, FGR, RAF1, LCK, PDGFRα |
|  | <20% inhibition | SRC, PDGFRα(V561D), BRAF(V600E), JAK1, PDGFRβ, PDGFRα(D842V), PDGFRα(T674I), JAK3, KIT(V560G), KIT KIT(T670I), BRAF, JAK2, KIT(D816V) |
| 200-123 at 0.01 μM | >20% inhibition | SRM, BRK, RAF1, BRAF(V600E), LCK |
|  | <20% inhibition | PDGFRα, JAK1, SRC, PDGFRα(V561D), FGR, PDGFRβ, PDGFRα(T674I), PDGFRα(D842V), KIT(V560G), JAK3, KIT(T670I), KIT, JAK2, KIT(D816V), BRAF |
| 200-139 at 0.01 μM | >20% inhibition | SRM, BRK, RAF1, LCK, PDGFRα |
|  | <20% inhibition | JAK1, PDGFRα(V561D), FGR, PDGFRβ, SRC, KIT(V560G), PDGFRα(D842V), BRAF(V600E), PDGFRα(T674I), KIT, KIT(T670I), JAK3, JAK2, KIT(D816V), BRAF |

Example 10

Cell growth assay with breast cancer cell line T-47D: T-47D (ATCC® HTB-133™) was purchased from American Type Culture Collection (ATCC, Manassas, Va.). T-47D cells grew in DMDM medium (Gibco, Life Technologies) supplemented with 10% FBS (Gibco, Life Technologies) (complete medium) a T-75 flask at 37° C. under 5% $CO_2$ with saturated humidity. When the cells were approximately 70-80% confluent, the culture medium was removed, the cell layer was rinsed with 10 mL Dulbecco's Phosphate-Buffered Saline (DPBS), and immediately following the treatment with 1 mL of 025% (w/v) Trypsin-EDTA solution at 37° C. for 5-15 min. A 9 mL aliquot of the complete medium was then gently dispersed over the surface of the cell layer for several times. The cell concentration was adjusted to $1 \times 10^4$ cells/mL with the complete medium. A 100 μL aliquot of the cell suspension was added to the well of a 96-well plate, and the plate was incubated overnight at 37° C. under 5% $CO_2$ with saturated humidity. On the next day, the medium in each well was aspirated and replaced with a 100

µL aliquot of pre-warmed complete medium at 37° C. in the presence or absence of the test compounds at various concentrations from 0-100 µM. The test compounds were dissolved in DMSO, and the final DMSO concentration in the cell culture was no more than 1%. The plate was incubated for 72 hours at 37° C. under 5% CO$_2$ with saturated humidity. At end of the cell culture, a 10 µL aliquot of PrestoBlue® Cell Viability reagent (ThermoFisher Scientific) was added into the well, and the plate was incubated at 37° C. for 30 min. The absorption at 570 and 600 nm were measured with a SpectraMax Microplate reader (Molecular Devices). The absorbance at 570 nm was normalized to that at 600 nm. The normalized absorbance at 570 nm was used for IC$_{50}$ calculation following the median-effect plot method (T. C. Chou, Pharmacol Rev 2006, 58: 621-681). The IC$_{50}$ values for 200-17, 200-73, 200-93b, 200-115, 200-117, 200-123, 200-139 and 200-149 were less than 20 µM, while the IC$_{50}$ value for 200-93a was greater than 20 µM.

It is understood that the examples and embodiments described herein are for illustrative purposes only and that various modifications or changes in light thereof will be suggested to persons skilled in the art and are to be included within the spirit and purview of this application and scope of appended claim. All publications, patents, and patent applications cited herein are hereby incorporated by reference.

We claim:
1. A compound of the following formula IV:

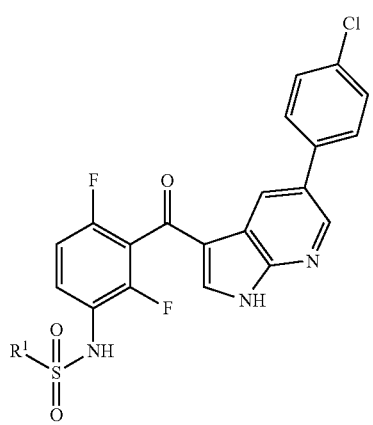

formula IV or a pharmaceutically acceptable salt, prodrug, or isomer thereof;
R$^1$ is a substituted lower alkyl or lower alkenyl, wherein the lower alkyl or lower alkenyl is substituted with one or more substituents selected from —OH, =O, and alkoxy.
2. The compound of claim 1, wherein said compound is a compound of structure 200-17:

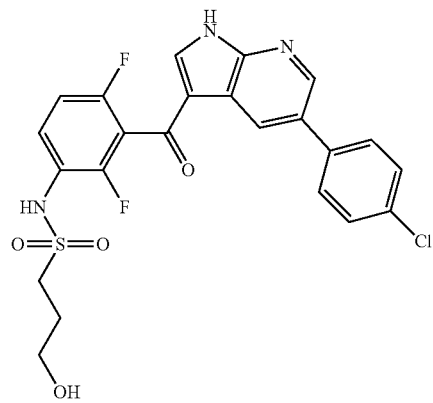

200-17 or a pharmaceutically acceptable salt, prodrug, or isomer thereof.
3. The compound of claim 1, wherein said compound is a compound of structure 200-73:

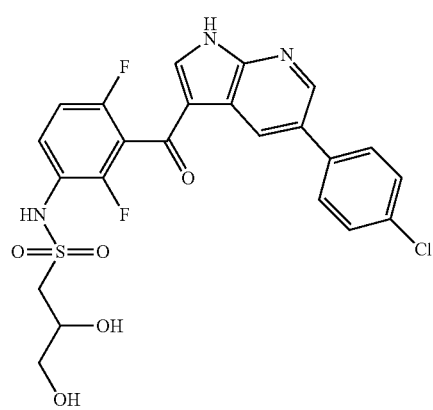

200-73 or a pharmaceutically acceptable salt, prodrug, or isomer thereof.
4. The compound of claim 1, wherein said compound is a compound of structure 200-115:

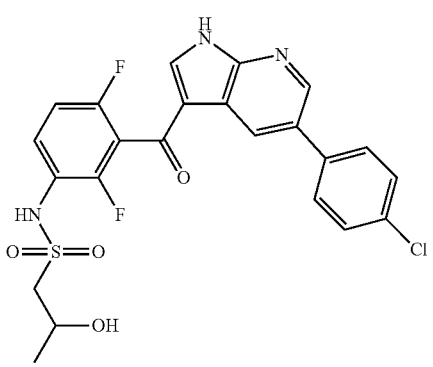

200-115 or a pharmaceutically acceptable salt, prodrug, or isomer thereof.
5. The compound of claim 1, wherein said compound is a compound of structure 200-117:

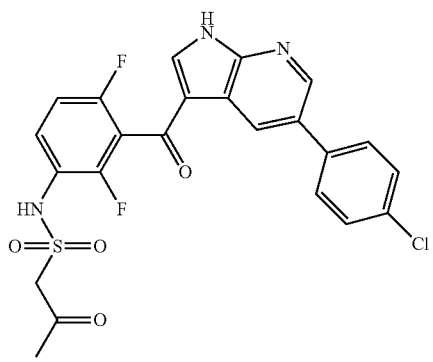

200-117 or a pharmaceutically acceptable salt, prodrug, or isomer thereof.

6. The compound of claim 1, wherein said compound is a compound of structure 200-123:

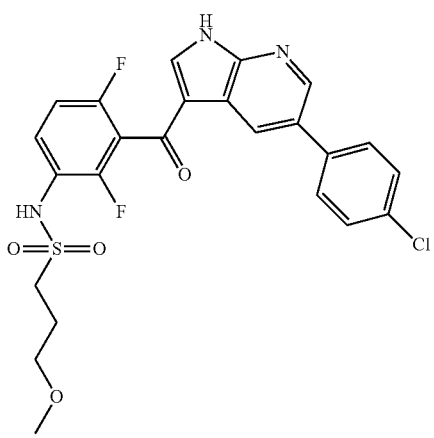

200-123 or a pharmaceutically acceptable salt, prodrug, or isomer thereof.

7. The compound of claim 1, wherein said compound is a compound of structure 200-139:

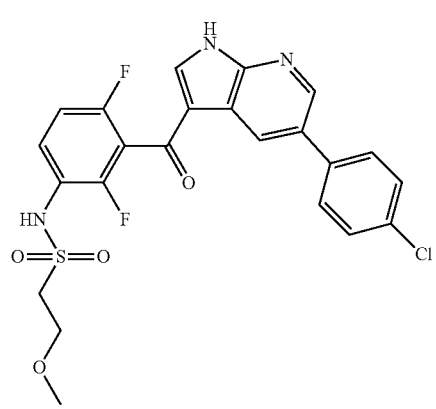

200-139 or a pharmaceutically acceptable salt, prodrug, or isomer thereof.

8. The compound of claim 1, wherein said compound is a compound of structure 200-149:

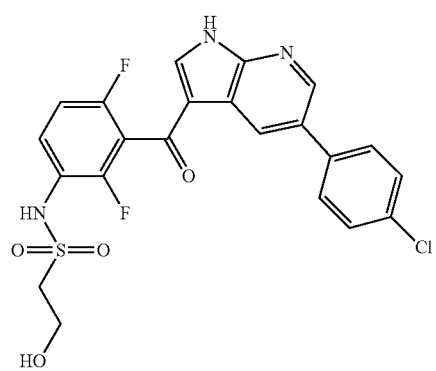

200-149 or a pharmaceutically acceptable salt, prodrug, or isomer thereof.

* * * * *